(12) United States Patent
Jackson

(10) Patent No.: US 8,475,498 B2
(45) Date of Patent: Jul. 2, 2013

(54) DYNAMIC STABILIZATION CONNECTING MEMBER WITH CORD CONNECTION

(76) Inventor: Roger P. Jackson, Prairie Village, KS (US)

( * ) Notice: Subject to any disclaimer, the term of this patent is extended or adjusted under 35 U.S.C. 154(b) by 1098 days.

(21) Appl. No.: 12/006,460

(22) Filed: Jan. 3, 2008

(65) Prior Publication Data

US 2008/0177317 A1    Jul. 24, 2008

Related U.S. Application Data

(60) Provisional application No. 60/922,465, filed on Apr. 9, 2007, provisional application No. 60/898,870, filed on Feb. 1, 2007, provisional application No. 60/880,969, filed on Jan. 18, 2007.

(51) Int. Cl.
*A61B 17/70* (2006.01)
(52) U.S. Cl.
USPC .......................................................... 606/254
(58) Field of Classification Search
USPC .................................. 606/246–279; 428/188
See application file for complete search history.

(56) References Cited

U.S. PATENT DOCUMENTS

| 854,956 | A | 5/1907 | Martin |
| 2,243,717 | A | 5/1941 | Moreira |
| 2,346,346 | A | 4/1944 | Anderson |
| 2,362,999 | A | 11/1944 | Elmer |
| 2,531,892 | A | 11/1950 | Reese |
| 2,813,450 | A | 11/1957 | Dzus |
| 3,013,244 | A | 12/1961 | Rudy |
| 3,236,275 | A | 2/1966 | Smith |
| 3,604,487 | A | 9/1971 | Gilbert |
| 3,640,416 | A | 2/1972 | Temple |
| 4,033,139 | A | 7/1977 | Frederick |
| 4,041,939 | A | 8/1977 | Hall |
| 4,190,091 | A | 2/1980 | Colognori |

(Continued)

FOREIGN PATENT DOCUMENTS

| CA | 2577436 | 6/2006 |
| DE | G9202745.8 | 4/1992 |

(Continued)

OTHER PUBLICATIONS

*EBI Omega 21* Brochure, EBI Spine Systems, pub. 1999.

(Continued)

*Primary Examiner* — Eduardo C Robert
*Assistant Examiner* — Steven Cotroneo
(74) *Attorney, Agent, or Firm* — John C. McMahon

(57) ABSTRACT

A dynamic fixation medical implant having at least two bone anchors includes a longitudinal connecting member assembly having at least one transition portion and cooperating outer sleeve, both the transition portion and sleeve being disposed between the two bone anchors. In a first embodiment, the transition portion includes a rigid length or rod having apertures therein for tying or otherwise attaching the rigid length to a second rigid length or to a flexible cord. Slender ties or cords extend through a plurality of apertures in the rigid lengths or are threaded, tied or plaited to the larger flexible cord or cable. In a second embodiment, a transition portion includes slender ties of a cord that are imbedded in a molded plastic of a more rigid member. The outer sleeve may include compression grooves. The sleeve surrounds the transition portion and extends between the pair of bone anchors, the sleeve being compressible in a longitudinal direction between the bone anchors.

42 Claims, 6 Drawing Sheets

U.S. PATENT DOCUMENTS

| | | | |
|---|---|---|---|
| 4,373,754 A | 2/1983 | Bollfrass et al. |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Barker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |

| | | | | | | |
|---|---|---|---|---|---|---|
| 6,110,172 | A | 8/2000 | Jackson | 6,572,618 B1 | 6/2003 | Morrison |
| 6,113,601 | A | 9/2000 | Tatar | 6,582,436 B1 | 6/2003 | Schlapfer et al. |
| 6,117,137 | A | 9/2000 | Halm et al. | 6,582,466 B1 | 6/2003 | Gauchet |
| 6,132,431 | A | 10/2000 | Nilsson et al. | 6,585,740 B2 | 7/2003 | Schlapfer et al. |
| 6,132,432 | A | 10/2000 | Richelsoph | 6,595,992 B1 | 7/2003 | Wagner et al. |
| 6,132,434 | A | 10/2000 | Sherman et al. | 6,595,993 B2 | 7/2003 | Donno et al. |
| 6,136,002 | A | 10/2000 | Shih et al. | 6,599,294 B2 | 7/2003 | Fuss et al. |
| 6,139,549 | A | 10/2000 | Keller | 6,610,063 B2 | 8/2003 | Kumar et al. |
| 6,143,032 | A | 11/2000 | Schafer et al. | 6,613,050 B1 | 9/2003 | Wagner et al. |
| 6,146,383 | A | 11/2000 | Studer et al. | 6,616,667 B1 | 9/2003 | Steiger et al. |
| 6,183,472 | B1 | 2/2001 | Lutz | 6,616,669 B2 | 9/2003 | Ogilvie et al. |
| 6,186,718 | B1 | 2/2001 | Fogard | 6,623,485 B2 | 9/2003 | Doubler et al. |
| 6,187,005 | B1 | 2/2001 | Brace et al. | 6,626,347 B2 | 9/2003 | Ng |
| 6,193,720 | B1 | 2/2001 | Yuan et al. | 6,626,907 B2 | 9/2003 | Campbell et al. |
| 6,214,012 | B1 | 4/2001 | Karpman et al. | 6,626,908 B2 | 9/2003 | Cooper et al. |
| RE37,161 | E | 5/2001 | Michelson et al. | 6,635,059 B2 | 10/2003 | Randall et al. |
| 6,224,596 | B1 | 5/2001 | Jackson | 6,635,060 B2 | 10/2003 | Hanson et al. |
| 6,224,598 | B1 | 5/2001 | Jackson | 6,648,885 B1 | 11/2003 | Friesem |
| 6,235,028 | B1 | 5/2001 | Brumfield et al. | 6,648,887 B2 | 11/2003 | Ashman |
| 6,235,034 | B1 | 5/2001 | Bray | 6,648,888 B1 | 11/2003 | Shluzas |
| 6,241,730 | B1 | 6/2001 | Alby | 6,652,526 B1 | 11/2003 | Arafiles |
| 6,248,105 | B1 | 6/2001 | Schlapfer et al. | 6,652,765 B1 | 11/2003 | Beaty |
| 6,248,107 | B1 | 6/2001 | Foley et al. | 6,656,179 B1 | 12/2003 | Schaefer et al. |
| 6,251,112 | B1 | 6/2001 | Jackson | 6,656,181 B2 | 12/2003 | Dixon et al. |
| 6,254,146 | B1 | 7/2001 | Church | 6,660,004 B2 | 12/2003 | Barker et al. |
| 6,254,602 | B1 | 7/2001 | Justis | 6,660,006 B2 | 12/2003 | Markworth et al. |
| 6,267,764 | B1 | 7/2001 | Elberg | 6,663,632 B1 | 12/2003 | Frigg |
| 6,267,765 | B1 | 7/2001 | Taylor et al. | 6,663,635 B2 | 12/2003 | Frigg et al. |
| 6,273,888 | B1 | 8/2001 | Justis | 6,673,073 B1 | 1/2004 | Schafer |
| 6,277,122 | B1 | 8/2001 | McGahan et al. | 6,676,661 B1 | 1/2004 | Martin Benlloch et al. |
| 6,280,442 | B1 | 8/2001 | Barker et al. | 6,679,833 B2 | 1/2004 | Smith et al. |
| 6,280,445 | B1 | 8/2001 | Morrison et al. | 6,682,529 B2 | 1/2004 | Stahurski |
| 6,287,308 | B1 | 9/2001 | Betz et al. | 6,682,530 B2 | 1/2004 | Dixon et al. |
| 6,287,311 | B1 | 9/2001 | Sherman et al. | 6,689,133 B2 | 2/2004 | Morrison et al. |
| 6,290,700 | B1 * | 9/2001 | Schmotzer ............... 606/263 | 6,689,134 B2 | 2/2004 | Ralph et al. |
| 6,296,642 | B1 | 10/2001 | Morrison et al. | 6,695,843 B2 | 2/2004 | Biedermann et al. |
| 6,296,643 | B1 | 10/2001 | Hopf et al. | 6,695,851 B2 | 2/2004 | Zdeblick et al. |
| 6,299,613 | B1 | 10/2001 | Ogilvie et al. | 6,699,249 B2 | 3/2004 | Schlapfer et al. |
| 6,302,888 | B1 | 10/2001 | Mellinger et al. | 6,706,045 B2 | 3/2004 | Lin et al. |
| 6,309,391 | B1 | 10/2001 | Crandall et al. | 6,712,818 B1 | 3/2004 | Michelson |
| 6,315,564 | B1 | 11/2001 | Levisman | 6,716,213 B2 | 4/2004 | Shitoto |
| 6,315,779 | B1 | 11/2001 | Morrison et al. | 6,716,214 B1 | 4/2004 | Jackson |
| 6,331,179 | B1 | 12/2001 | Freid et al. | 6,716,247 B2 | 4/2004 | Michelson |
| 6,355,040 | B1 | 3/2002 | Richelsoph et al. | 6,723,100 B2 | 4/2004 | Biedermann et al. |
| RE37,665 | E | 4/2002 | Ralph et al. | 6,730,093 B2 | 5/2004 | Saint Martin |
| 6,368,321 | B1 | 4/2002 | Jackson | 6,730,127 B2 | 5/2004 | Michelson |
| 6,371,957 | B1 | 4/2002 | Amrein et al. | 6,733,502 B2 | 5/2004 | Altarac et al. |
| 6,402,752 | B2 | 6/2002 | Schaffler-Wachter et al. | 6,736,816 B2 | 5/2004 | Ritland |
| 6,402,757 | B1 | 6/2002 | Moore et al. | 6,736,820 B2 | 5/2004 | Biedermann et al. |
| 6,440,133 | B1 | 8/2002 | Beale et al. | 6,740,086 B2 | 5/2004 | Richelsoph |
| 6,440,137 | B1 | 8/2002 | Horvath et al. | 6,743,231 B1 | 6/2004 | Gray et al. |
| 6,443,956 | B1 | 9/2002 | Ray | 6,746,449 B2 | 6/2004 | Jones et al. |
| 6,451,021 | B1 | 9/2002 | Ralph et al. | 6,746,454 B2 | 6/2004 | Winterbottom et al. |
| 6,471,703 | B1 | 10/2002 | Ashman | 6,755,829 B1 | 6/2004 | Bono et al. |
| 6,471,705 | B1 | 10/2002 | Biedermann et al. | 6,755,835 B2 | 6/2004 | Schultheiss et al. |
| 6,478,801 | B1 | 11/2002 | Ralph et al. | 6,755,836 B1 | 6/2004 | Lewis |
| 6,485,491 | B1 | 11/2002 | Farris et al. | 6,761,723 B2 | 7/2004 | Butterman et al. |
| 6,485,492 | B1 | 11/2002 | Halm et al. | 6,767,351 B2 | 7/2004 | Orbay et al. |
| 6,485,494 | B1 | 11/2002 | Haider | 6,770,075 B2 | 8/2004 | Howland |
| 6,488,681 | B2 | 12/2002 | Martin et al. | 6,778,861 B1 | 8/2004 | Liebrecht et al. |
| 6,508,818 | B2 | 1/2003 | Steiner et al. | 6,780,186 B2 | 8/2004 | Errico et al. |
| 6,511,484 | B2 | 1/2003 | Torode et al. | 6,783,527 B2 | 8/2004 | Drewry et al. |
| 6,520,962 | B1 | 2/2003 | Taylor et al. | 6,790,208 B2 | 9/2004 | Oribe et al. |
| 6,527,804 | B1 | 3/2003 | Gauchet et al. | 6,790,209 B2 | 9/2004 | Beale et al. |
| 6,530,929 | B1 | 3/2003 | Justis et al. | 6,802,844 B2 | 10/2004 | Ferree |
| 6,533,786 | B1 | 3/2003 | Needham et al. | 6,827,719 B2 | 12/2004 | Ralph et al. |
| 6,539,826 | B1 | 4/2003 | Oesterle et al. | 6,830,571 B2 | 12/2004 | Lenke et al. |
| 6,540,749 | B2 | 4/2003 | Schafer et al. | 6,835,196 B2 | 12/2004 | Biedermann et al. |
| 6,547,790 | B2 | 4/2003 | Harkey, III et al. | 6,837,889 B2 | 1/2005 | Shluzas |
| 6,551,320 | B2 | 4/2003 | Liebermann | 6,840,940 B2 | 1/2005 | Ralph et al. |
| 6,551,323 | B2 | 4/2003 | Doubler et al. | 6,843,791 B2 | 1/2005 | Serhan |
| 6,554,831 | B1 | 4/2003 | Rivard et al. | 6,857,343 B2 | 2/2005 | Easterbrooks et al. |
| 6,554,832 | B2 | 4/2003 | Shluzas | 6,858,031 B2 | 2/2005 | Morrison et al. |
| 6,554,834 | B2 | 4/2003 | Crozet et al. | 6,869,432 B2 | 3/2005 | Schlapfer et al. |
| 6,558,387 | B2 | 5/2003 | Errico et al. | 6,869,433 B2 | 3/2005 | Glascott |
| 6,562,038 | B1 | 5/2003 | Morrison | 6,872,208 B1 | 3/2005 | McBride et al. |
| 6,562,040 | B1 | 5/2003 | Wagner | 6,896,676 B2 | 5/2005 | Zubok et al. |
| 6,565,565 | B1 | 5/2003 | Yuan et al. | 6,932,817 B2 | 8/2005 | Baynham et al. |
| 6,565,567 | B1 | 5/2003 | Haider | 6,932,820 B2 | 8/2005 | Osman |

| | | |
|---|---|---|
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| 7,033,394 B2 * | 4/2006 | Michelson ............ 623/17.11 |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,282,064 B2 | 10/2007 | Chin |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,476,238 B2 | 1/2009 | Panjabi |
| 7,491,208 B2 | 2/2009 | Pond, Jr. et al. |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,621,912 B2 | 11/2009 | Harms et al. |
| 7,621,940 B2 | 11/2009 | Harms et al. |
| 7,625,393 B2 | 12/2009 | Fallin et al. |
| 7,632,292 B2 | 12/2009 | Sengupta et al. |
| 7,641,673 B2 | 1/2010 | LeCouedic et al. |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,682,375 B2 | 3/2010 | Ritland |
| 7,695,496 B2 | 4/2010 | Labrom et al. |
| 7,695,498 B2 | 4/2010 | Ritland |
| 7,695,514 B2 | 4/2010 | Kwak |
| 7,763,048 B2 | 7/2010 | Fortin et al. |
| 7,763,052 B2 | 7/2010 | Jahng |
| 7,766,941 B2 | 8/2010 | Paul |
| 7,766,942 B2 | 8/2010 | Patterson et al. |
| 7,766,943 B1 | 8/2010 | Fallin et al. |
| 7,776,071 B2 | 8/2010 | Fortin et al. |
| 7,776,075 B2 | 8/2010 | Bruneau et al. |
| 7,785,349 B2 | 8/2010 | Walder et al. |
| 7,785,351 B2 | 8/2010 | Gordon et al. |
| 7,794,480 B2 | 9/2010 | Gordon et al. |
| 7,806,913 B2 | 10/2010 | Fanger et al. |
| 7,811,309 B2 | 10/2010 | Timm et al. |
| 7,815,663 B2 | 10/2010 | Trieu |
| 7,815,664 B2 | 10/2010 | Sherman et al. |
| 7,815,665 B2 * | 10/2010 | Jahng et al. ............ 606/263 |
| 2001/0001119 A1 | 5/2001 | Lombardo |
| 2001/0010000 A1 | 7/2001 | Gertzbein |
| 2001/0023350 A1 | 9/2001 | Choi |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0095153 A1 | 7/2002 | Jones et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208204 A1 | 11/2003 | Bailey et al. |
| 2003/0216735 A1 | 11/2003 | Altarac et al. |

| | | |
|---|---|---|
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172025 A1 | 9/2004 | Drewry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0236327 A1* | 11/2004 | Paul et al. ............... 606/61 |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0080415 A1 | 4/2005 | Keyer et al. |
| 2005/0085812 A1 | 4/2005 | Sherman |
| 2005/0085813 A1 | 4/2005 | Spitler et al. |
| 2005/0085815 A1* | 4/2005 | Harms et al. ............... 606/61 |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1* | 7/2005 | Jahng ............... 606/61 |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1* | 12/2005 | Trieu et al. ............... 606/61 |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |

| | | | | | | |
|---|---|---|---|---|---|---|
| 2006/0052784 A1 | 3/2006 | Dant et al. | | 2006/0217719 A1 | 9/2006 | Albert et al. |
| 2006/0052786 A1 | 3/2006 | Dant et al. | | 2006/0229608 A1 | 10/2006 | Foster |
| 2006/0058788 A1 | 3/2006 | Hammer et al. | | 2006/0229609 A1 | 10/2006 | Wang |
| 2006/0058790 A1 | 3/2006 | Carl et al. | | 2006/0229612 A1 | 10/2006 | Rothman |
| 2006/0064090 A1 | 3/2006 | Park | | 2006/0229613 A1 | 10/2006 | Timm |
| 2006/0064091 A1 | 3/2006 | Ludwig et al. | | 2006/0229614 A1 | 10/2006 | Foley et al. |
| 2006/0064092 A1 | 3/2006 | Howland | | 2006/0229615 A1 | 10/2006 | Abdou |
| 2006/0069390 A1 | 3/2006 | Frigg | | 2006/0235389 A1 | 10/2006 | Albert et al. |
| 2006/0074419 A1 | 4/2006 | Taylor et al. | | 2006/0235392 A1 | 10/2006 | Hammer et al. |
| 2006/0079894 A1 | 4/2006 | Colleran et al. | | 2006/0235393 A1 | 10/2006 | Bono et al. |
| 2006/0079895 A1 | 4/2006 | McLeer | | 2006/0241593 A1 | 10/2006 | Sherman et al. |
| 2006/0079896 A1 | 4/2006 | Kwak | | 2006/0241595 A1 | 10/2006 | Molz, IV et al. |
| 2006/0079898 A1 | 4/2006 | Ainsworth | | 2006/0241599 A1 | 10/2006 | Konieczynski et al. |
| 2006/0079899 A1 | 4/2006 | Ritland | | 2006/0241600 A1 | 10/2006 | Ensign et al. |
| 2006/0084977 A1 | 4/2006 | Liebermann | | 2006/0241769 A1 | 10/2006 | Gordon |
| 2006/0084981 A1 | 4/2006 | Shluzas | | 2006/0241771 A1 | 10/2006 | Gordon |
| 2006/0084982 A1 | 4/2006 | Kim | | 2006/0247624 A1 | 11/2006 | Banouskou et al. |
| 2006/0084983 A1 | 4/2006 | Kim | | 2006/0247630 A1 | 11/2006 | Iott et al. |
| 2006/0084984 A1 | 4/2006 | Kim | | 2006/0247631 A1 | 11/2006 | Ahn et al. |
| 2006/0084985 A1 | 4/2006 | Kim | | 2006/0247632 A1 | 11/2006 | Winslow |
| 2006/0084987 A1 | 4/2006 | Kim | | 2006/0247633 A1 | 11/2006 | Winslow |
| 2006/0084988 A1 | 4/2006 | Kim | | 2006/0247635 A1 | 11/2006 | Gordon |
| 2006/0084989 A1 | 4/2006 | Dickinson et al. | | 2006/0247636 A1 | 11/2006 | Yuan et al. |
| 2006/0084991 A1 | 4/2006 | Borgstrom | | 2006/0247637 A1 | 11/2006 | Colleran |
| 2006/0084993 A1 | 4/2006 | Landry et al. | | 2006/0247779 A1 | 11/2006 | Gordon |
| 2006/0084995 A1 | 4/2006 | Biedermann et al. | | 2006/0263201 A1 | 11/2006 | Harman |
| 2006/0085069 A1 | 4/2006 | Kim | | 2006/0264933 A1 | 11/2006 | Baker et al. |
| 2006/0089643 A1 | 4/2006 | Mujwid | | 2006/0264934 A1 | 11/2006 | Fallin |
| 2006/0089644 A1 | 4/2006 | Felix | | 2006/0264935 A1 | 11/2006 | White |
| 2006/0095037 A1 | 5/2006 | Jones et al. | | 2006/0264936 A1 | 11/2006 | Partin et al. |
| 2006/0106380 A1 | 5/2006 | Colleran et al. | | 2006/0264937 A1 | 11/2006 | White |
| 2006/0106381 A1 | 5/2006 | Ferree | | 2006/0264940 A1 | 11/2006 | Hartmannt |
| 2006/0106383 A1 | 5/2006 | Biedermann et al. | | 2006/0264942 A1 | 11/2006 | Lim et al. |
| 2006/0111714 A1 | 5/2006 | Foley | | 2006/0264962 A1 | 11/2006 | Chin et al. |
| 2006/0111715 A1 | 5/2006 | Jackson | | 2006/0276787 A1 | 12/2006 | Zubok et al. |
| 2006/0116677 A1 | 6/2006 | Burd et al. | | 2006/0276789 A1 | 12/2006 | Jackson |
| 2006/0122597 A1 | 6/2006 | Jojnes et al. | | 2006/0276791 A1 | 12/2006 | Shluzas |
| 2006/0122599 A1 | 6/2006 | Drewry | | 2006/0276792 A1 | 12/2006 | Ensign et al. |
| 2006/0129147 A1 | 6/2006 | Biedermann et al. | | 2006/0282074 A1 | 12/2006 | Renaud et al. |
| 2006/0129149 A1 | 6/2006 | Iott et al. | | 2006/0282075 A1 | 12/2006 | Labrom |
| 2006/0129239 A1 | 6/2006 | Kwak | | 2006/0282076 A1 | 12/2006 | Labrom |
| 2006/0142758 A1 | 6/2006 | Petit | | 2006/0282077 A1 | 12/2006 | Labrom |
| 2006/0142760 A1 | 6/2006 | McDonnell | | 2006/0282078 A1 | 12/2006 | Labrom |
| 2006/0142761 A1 | 6/2006 | Landry et al. | | 2006/0282079 A1 | 12/2006 | Labrom |
| 2006/0149228 A1 | 7/2006 | Schlapfer | | 2006/0282080 A1 | 12/2006 | Albert |
| 2006/0149229 A1 | 7/2006 | Kwak | | 2006/0293657 A1 | 12/2006 | Hartmann |
| 2006/0149232 A1 | 7/2006 | Sasing | | 2006/0293659 A1 | 12/2006 | Alvarez |
| 2006/0149238 A1 | 7/2006 | Sherman et al. | | 2006/0293663 A1 | 12/2006 | Walkenhorst |
| 2006/0149241 A1 | 7/2006 | Richelsoph et al. | | 2006/0293665 A1 | 12/2006 | Shluzas |
| 2006/0149244 A1 | 7/2006 | Amrein et al. | | 2006/0293666 A1 | 12/2006 | Matthis et al. |
| 2006/0155277 A1 | 7/2006 | Metz-Stavenhagen | | 2007/0005062 A1 | 1/2007 | Lange |
| 2006/0155278 A1 | 7/2006 | Warnick | | 2007/0005063 A1 | 1/2007 | Bruneau |
| 2006/0161152 A1 | 7/2006 | Ensign et al. | | 2007/0005137 A1 | 1/2007 | Kwak |
| 2006/0167454 A1 | 7/2006 | Ludwig et al. | | 2007/0016188 A1 | 1/2007 | Boehm, Jr. et al. |
| 2006/0167455 A1 | 7/2006 | Clement et al. | | 2007/0016190 A1 | 1/2007 | Martinez |
| 2006/0173454 A1 | 8/2006 | Spitler et al. | | 2007/0016193 A1 | 1/2007 | Ritland |
| 2006/0173456 A1 | 8/2006 | Hawkes et al. | | 2007/0016194 A1 | 1/2007 | Shaolian et al. |
| 2006/0184171 A1 | 8/2006 | Biedermann | | 2007/0016198 A1 | 1/2007 | Boehm, Jr. et al. |
| 2006/0184180 A1 | 8/2006 | Augostino | | 2007/0016199 A1 | 1/2007 | Boehm, Jr. et al. |
| 2006/0189983 A1 | 8/2006 | Fallin | | 2007/0021750 A1 | 1/2007 | Shluzas et al. |
| 2006/0189984 A1 | 8/2006 | Fallin | | 2007/0043355 A1 | 2/2007 | Bette et al. |
| 2006/0189985 A1 | 8/2006 | Lewis | | 2007/0043356 A1 | 2/2007 | Timm |
| 2006/0195090 A1 | 8/2006 | Suddaby | | 2007/0043357 A1 | 2/2007 | Kirschman |
| 2006/0195093 A1 | 8/2006 | Jahng | | 2007/0043358 A1 | 2/2007 | Molz, IV et al. |
| 2006/0195098 A1 | 8/2006 | Schumacher | | 2007/0043359 A1 | 2/2007 | Altarac et al. |
| 2006/0200128 A1 | 9/2006 | Mueller | | 2007/0043364 A1 | 2/2007 | Cawley et al. |
| 2006/0200130 A1 | 9/2006 | Hawkins | | 2007/0049931 A1 | 3/2007 | Justis et al. |
| 2006/0200131 A1 | 9/2006 | Chao et al. | | 2007/0049933 A1 | 3/2007 | Ahn et al. |
| 2006/0200132 A1 | 9/2006 | Chao et al. | | 2007/0049936 A1 | 3/2007 | Colleran |
| 2006/0200135 A1 | 9/2006 | Sherman et al. | | 2007/0055235 A1 | 3/2007 | Janowski et al. |
| 2006/0200138 A1 | 9/2006 | Michelson | | 2007/0055236 A1 | 3/2007 | Hudgins |
| 2006/0200139 A1 | 9/2006 | Michelson | | 2007/0055238 A1 | 3/2007 | Biedermann et al. |
| 2006/0200149 A1 | 9/2006 | Hoy et al. | | 2007/0055239 A1 | 3/2007 | Sweeney et al. |
| 2006/0210494 A1 | 9/2006 | Rabiei et al. | | 2007/0055240 A1 | 3/2007 | Matthis et al. |
| 2006/0212033 A1 | 9/2006 | Rothman | | 2007/0055241 A1 | 3/2007 | Matthis et al. |
| 2006/0212034 A1 | 9/2006 | Triplett et al. | | 2007/0055242 A1 | 3/2007 | Bailly |
| 2006/0217713 A1 | 9/2006 | Serhan et al. | | 2007/0055244 A1 | 3/2007 | Jackson |
| 2006/0217714 A1 | 9/2006 | Serhan et al. | | 2007/0055247 A1 | 3/2007 | Jahng |
| 2006/0217716 A1 | 9/2006 | Baker et al. | | 2007/0073289 A1 | 3/2007 | Kwak |

| | | | | | |
|---|---|---|---|---|---|
| 2007/0073290 A1 | 3/2007 | Boehm, Jr. | 2007/0270814 A1 | 11/2007 | Lim et al. |
| 2007/0073291 A1 | 3/2007 | Cordaro et al. | 2007/0270815 A1 | 11/2007 | Johnson et al. |
| 2007/0073293 A1 | 3/2007 | Martz | 2007/0270821 A1 | 11/2007 | Trieu et al. |
| 2007/0073294 A1 | 3/2007 | Chin et al. | 2007/0270830 A1 | 11/2007 | Morrison |
| 2007/0078460 A1 | 4/2007 | Frigg et al. | 2007/0270831 A1 | 11/2007 | Dewey et al. |
| 2007/0078461 A1 | 4/2007 | Shluzas | 2007/0270832 A1 | 11/2007 | Moore |
| 2007/0083199 A1 | 4/2007 | Baccelli | 2007/0270835 A1 | 11/2007 | Wisnewski |
| 2007/0088357 A1 | 4/2007 | Johnson et al. | 2007/0270837 A1 | 11/2007 | Eckhardt et al. |
| 2007/0088359 A1 | 4/2007 | Woods et al. | 2007/0270838 A1 | 11/2007 | Bruneau et al. |
| 2007/0093813 A1 | 4/2007 | Callahan et al. | 2007/0270839 A1 | 11/2007 | Jeon et al. |
| 2007/0093814 A1 | 4/2007 | Callahan, II et al. | 2007/0270843 A1 | 11/2007 | Matthis et al. |
| 2007/0093815 A1 | 4/2007 | Callahan, II et al. | 2007/0276380 A1 | 11/2007 | Jahng et al. |
| 2007/0093817 A1 | 4/2007 | Barrus et al. | 2007/0288004 A1 | 12/2007 | Alvarez |
| 2007/0093818 A1 | 4/2007 | Biedermann et al. | 2007/0288008 A1 | 12/2007 | Park |
| 2007/0093819 A1 | 4/2007 | Albert | 2007/0288009 A1 | 12/2007 | Brown et al. |
| 2007/0093824 A1 | 4/2007 | Hestad et al. | 2007/0288011 A1 | 12/2007 | Logan |
| 2007/0093826 A1 | 4/2007 | Hawkes et al. | 2007/0288012 A1 | 12/2007 | Colleran et al. |
| 2007/0093827 A1 | 4/2007 | Warnick | 2008/0009862 A1 | 1/2008 | Hoffman |
| 2007/0093828 A1 | 4/2007 | Abdou | 2008/0009864 A1 | 1/2008 | Forton et al. |
| 2007/0093831 A1 | 4/2007 | Abdelgany et al. | 2008/0015578 A1 | 1/2008 | Erickson et al. |
| 2007/0093833 A1 | 4/2007 | Kuiper et al. | 2008/0015579 A1 | 1/2008 | Whipple |
| 2007/0100341 A1 | 5/2007 | Reglos et al. | 2008/0015580 A1 | 1/2008 | Chao |
| 2007/0118117 A1 | 5/2007 | Altarac et al. | 2008/0015584 A1 | 1/2008 | Richelsoph |
| 2007/0118118 A1 | 5/2007 | Kwak et al. | 2008/0015586 A1 | 1/2008 | Krishna et al. |
| 2007/0118119 A1 | 5/2007 | Hestad | 2008/0021454 A1 | 1/2008 | Chao et al. |
| 2007/0118122 A1 | 5/2007 | Butler et al. | 2008/0021455 A1 | 1/2008 | Chao et al. |
| 2007/0118123 A1 | 5/2007 | Strausbaugh et al. | 2008/0021458 A1 | 1/2008 | Lim |
| 2007/0118124 A1 | 5/2007 | Biedermann et al. | 2008/0021459 A1 | 1/2008 | Lim |
| 2007/0123862 A1 | 5/2007 | Warnick | 2008/0021462 A1 | 1/2008 | Trieu |
| 2007/0123864 A1 | 5/2007 | Walder et al. | 2008/0021464 A1 | 1/2008 | Morin et al. |
| 2007/0123865 A1 | 5/2007 | Schlapfer et al. | 2008/0021465 A1 | 1/2008 | Shadduck et al. |
| 2007/0123866 A1 | 5/2007 | Gerbec et al. | 2008/0021466 A1 | 1/2008 | Shadduck et al. |
| 2007/0123867 A1 | 5/2007 | Kirschman | 2008/0021473 A1 | 1/2008 | Butler et al. |
| 2007/0123870 A1 | 5/2007 | Jeon et al. | 2008/0027432 A1 | 1/2008 | Strauss et al. |
| 2007/0123871 A1 | 5/2007 | Jahng | 2008/0033435 A1 | 2/2008 | Studer et al. |
| 2007/0129729 A1* | 6/2007 | Petit et al. ............... 606/61 | 2008/0039838 A1 | 2/2008 | Landry et al. |
| 2007/0135815 A1 | 6/2007 | Gerbec et al. | 2008/0039843 A1 | 2/2008 | Abdou |
| 2007/0161986 A1 | 7/2007 | Levy | 2008/0045951 A1 | 2/2008 | Fanger et al. |
| 2007/0161991 A1 | 7/2007 | Altarac et al. | 2008/0045955 A1 | 2/2008 | Berrevoets et al. |
| 2007/0161994 A1 | 7/2007 | Lowrey et al. | 2008/0045957 A1 | 2/2008 | Landry et al. |
| 2007/0161995 A1 | 7/2007 | Trautwein et al. | 2008/0051780 A1 | 2/2008 | Vaidya et al. |
| 2007/0161996 A1 | 7/2007 | Biedermann et al. | 2008/0051787 A1 | 2/2008 | Remington et al. |
| 2007/0161997 A1 | 7/2007 | Thramann et al. | 2008/0058811 A1 | 3/2008 | Alleyne et al. |
| 2007/0161999 A1 | 7/2007 | Biedermann et al. | 2008/0058812 A1 | 3/2008 | Zehnder |
| 2007/0167948 A1 | 7/2007 | Abdou | 2008/0065071 A1 | 3/2008 | Park |
| 2007/0167949 A1 | 7/2007 | Altarac et al. | 2008/0065073 A1 | 3/2008 | Perriello et al. |
| 2007/0173818 A1 | 7/2007 | Hestad et al. | 2008/0065075 A1 | 3/2008 | Dant |
| 2007/0173819 A1 | 7/2007 | Sandlin | 2008/0065077 A1 | 3/2008 | Ferree |
| 2007/0173820 A1 | 7/2007 | Trieu | 2008/0065079 A1 | 3/2008 | Bruneau et al. |
| 2007/0173822 A1 | 7/2007 | Bruneau et al. | 2008/0071273 A1 | 3/2008 | Hawkes et al. |
| 2007/0173828 A1 | 7/2007 | Firkins et al. | 2008/0071274 A1 | 3/2008 | Ensign |
| 2007/0173832 A1 | 7/2007 | Tebbe et al. | 2008/0071277 A1 | 3/2008 | Warnick |
| 2007/0191839 A1 | 8/2007 | Justis et al. | 2008/0077139 A1 | 3/2008 | Landry et al. |
| 2007/0191841 A1 | 8/2007 | Justis et al. | 2008/0086131 A1 | 4/2008 | Daly et al. |
| 2007/0191846 A1 | 8/2007 | Bruneau et al. | 2008/0086132 A1 | 4/2008 | Biedermann et al. |
| 2007/0198014 A1 | 8/2007 | Graf et al. | 2008/0091214 A1 | 4/2008 | Richelsoph |
| 2007/0208344 A1 | 9/2007 | Young | 2008/0097431 A1 | 4/2008 | Vessa |
| 2007/0213720 A1 | 9/2007 | Gordon et al. | 2008/0097434 A1 | 4/2008 | Moumene et al. |
| 2007/0225707 A1 | 9/2007 | Wisnewski et al. | 2008/0097441 A1 | 4/2008 | Hayes et al. |
| 2007/0225708 A1 | 9/2007 | Biedermann et al. | 2008/0097457 A1 | 4/2008 | Warnick |
| 2007/0225710 A1 | 9/2007 | Jahng et al. | 2008/0108992 A1 | 5/2008 | Barry et al. |
| 2007/0225711 A1 | 9/2007 | Ensign | 2008/0119858 A1 | 5/2008 | Potash |
| 2007/0233064 A1 | 10/2007 | Holt | 2008/0125777 A1 | 5/2008 | Veldman et al. |
| 2007/0233073 A1 | 10/2007 | Wisnewski et al. | 2008/0125787 A1 | 5/2008 | Doubler et al. |
| 2007/0233075 A1 | 10/2007 | Dawson | 2008/0132952 A1 | 6/2008 | Malandain et al. |
| 2007/0233078 A1 | 10/2007 | Justis et al. | 2008/0140075 A1 | 6/2008 | Ensign et al. |
| 2007/0233080 A1 | 10/2007 | Na et al. | 2008/0140076 A1 | 6/2008 | Jackson |
| 2007/0233085 A1 | 10/2007 | Biedermann et al. | 2008/0140133 A1 | 6/2008 | Allard et al. |
| 2007/0233086 A1 | 10/2007 | Harms et al. | 2008/0147122 A1 | 6/2008 | Jackson |
| 2007/0233087 A1 | 10/2007 | Schlapfer | 2008/0154307 A1 | 6/2008 | Colleran et al. |
| 2007/0233092 A1 | 10/2007 | Falahee | 2008/0161854 A1 | 7/2008 | Bae et al. |
| 2007/0233094 A1 | 10/2007 | Colleran et al. | 2008/0161859 A1 | 7/2008 | Nilsson |
| 2007/0233095 A1 | 10/2007 | Schlaepfer | 2008/0161863 A1 | 7/2008 | Arnold et al. |
| 2007/0250061 A1 | 10/2007 | Chin et al. | 2008/0167687 A1 | 7/2008 | Colleran et al. |
| 2007/0260246 A1 | 11/2007 | Biedermann | 2008/0177316 A1 | 7/2008 | Bergeronk et al. |
| 2007/0270806 A1 | 11/2007 | Foley et al. | 2008/0177317 A1 | 7/2008 | Jackson |
| 2007/0270807 A1 | 11/2007 | Armstrong et al. | 2008/0177319 A1 | 7/2008 | Schwab |
| 2007/0270810 A1 | 11/2007 | Sanders | 2008/0177321 A1 | 7/2008 | Drewry et al. |
| 2007/0270813 A1 | 11/2007 | Garamszegi | 2008/0177322 A1 | 7/2008 | Davis et al. |

| | | |
|---|---|---|
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Walder et al. |
| 2008/0234736 A1 | 9/2008 | Trieu et al. |
| 2008/0234737 A1 | 9/2008 | Boschert |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0243188 A1 | 10/2008 | Walder |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262552 A1 | 10/2008 | Kim |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0294195 A1 | 11/2008 | Egli et al. |
| 2008/0294196 A1 | 11/2008 | Egli et al. |
| 2008/0294197 A1 | 11/2008 | Egli et al. |
| 2008/0300630 A1 | 12/2008 | Bohnema et al. |
| 2008/0300633 A1 | 12/2008 | Jackson |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2008/0319482 A1 * | 12/2008 | Jackson ............ 606/246 |
| 2009/0005817 A1 | 1/2009 | Friedrich et al. |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hestad et al. |
| 2009/0030465 A1 | 1/2009 | Altarac et al. |
| 2009/0036924 A1 | 2/2009 | Egli et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088782 A1 | 4/2009 | Moumene et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durward et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177232 A1 | 7/2009 | Kiester |
| 2009/0192548 A1 | 7/2009 | Jeon et al. |
| 2009/0198281 A1 | 8/2009 | Rice et al. |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | Lehuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0299411 A1 | 12/2009 | Laskowitz et al. |
| 2009/0318968 A1 | 12/2009 | Duggal et al. |
| 2009/0318971 A1 | 12/2009 | Egli et al. |
| 2009/0326582 A1 | 12/2009 | Songer et al. |
| 2009/0326583 A1 | 12/2009 | Moumene et al. |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087865 A1 | 4/2010 | Biedermann et al. |
| 2010/0094348 A1 | 4/2010 | Biedermann et al. |
| 2010/0198261 A1 | 8/2010 | Trieu et al. |
| 2010/0198269 A1 | 8/2010 | Taylor et al. |
| 2010/0204736 A1 | 8/2010 | Biedermann et al. |
| 2010/0211104 A1 | 8/2010 | Moumene et al. |
| 2010/0222819 A1 | 9/2010 | Timm et al. |
| 2010/0228292 A1 | 9/2010 | Arnold et al. |
| 2010/0249843 A1 | 9/2010 | Wegrzyn, III |
| 2010/0256682 A1 | 10/2010 | Fallin et al. |
| 2010/0262187 A1 | 10/2010 | Marik et al. |
| 2010/0262190 A1 | 10/2010 | Ballard et al. |
| 2010/0274285 A1 | 10/2010 | Rouleau |
| 2010/0274287 A1 | 10/2010 | Rouleau et al. |
| 2010/0274288 A1 | 10/2010 | Prevost et al. |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |

| | | |
|---|---|---|
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 2365345 | 2/2002 |
| GB | 2382304 | 5/2003 |
| JP | 10277070 | 10/1998 |
| JP | 2000325358 | 3/2000 |
| JP | 2000325358 | 11/2000 |
| SU | 313538 | 10/1971 |
| WO | WO92/03100 | 3/1992 |
| WO | WO94/10927 | 5/1994 |
| WO | WO94/26191 | 11/1994 |
| WO | WO96/41582 | 12/1996 |
| WO | WO9641582 | 12/1996 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/013839 | 2/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/087121 * | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | WO2006/045094 | 4/2006 |
| WO | WO2006/066685 | 6/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/124249 | 11/2007 |
| WO | WO2007/130835 | 11/2007 |
| WO | WO2007/130840 | 11/2007 |
| WO | WO2007/130941 | 11/2007 |
| WO | WO2007124249 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.
*Spine,* Lipcott, Williams & Wilkins, Inc. vol. 24, No. 15, p. 1495.
Brochure of Tyco/Healthcare/Surgical Dynamics on Spiral Radius 90D, Publication Date: Sep. 2001, pp. 1-8.
Brochure of Sofamor Danek the Spine Specialist, TSRH, Pedicle Screw Spinal System, Publication Date: Jan. 23, 1995.
Brochure of Spinal Concepts, an Abbott Laboratories Company, Pathfinder, Minimally Invasive Pedicle Fixation System, Publication Date: Nov. 2003.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of Spineline, Current Concepts, Minimally Invasive Posterior Spinal Decompression and Fusion Procedures, Publication Date: Sep./Oct. 2003.
Brochure of Zimmer Spine, Inc., Dynesys® LIS Less Invasive Surgery, The Dynamic Stabilization System, Publication Date: 2005.
VLS System Variable Locking Screw Brochure, Interpore Cross International,1999.

* cited by examiner

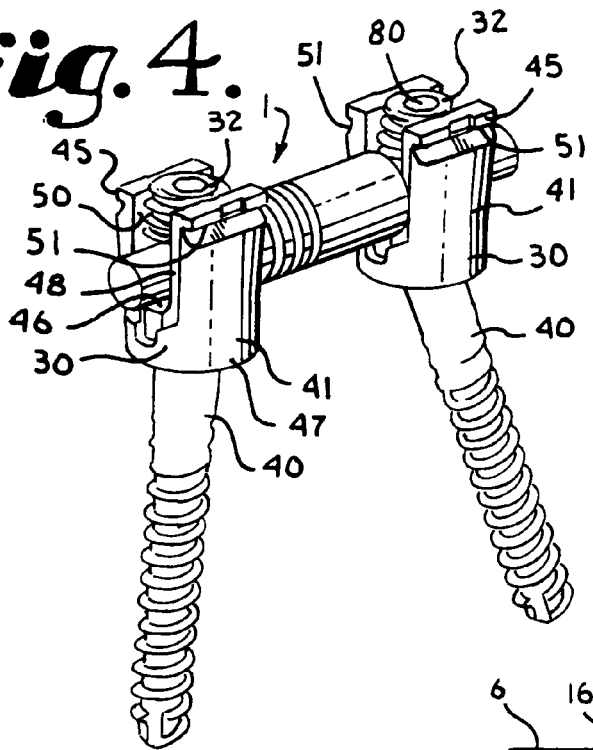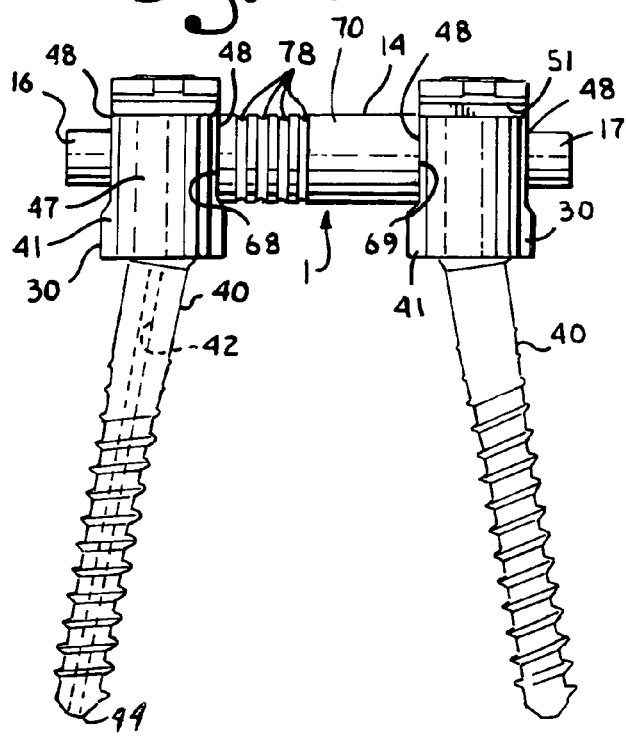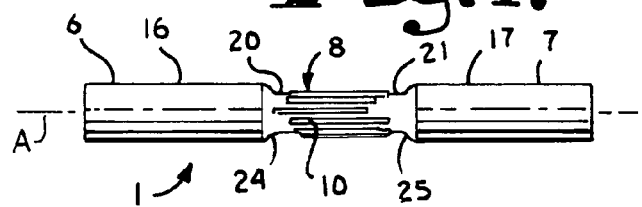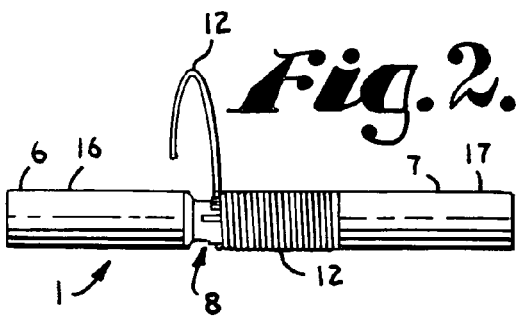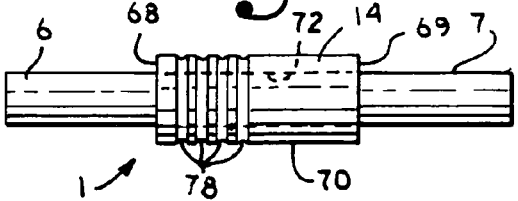

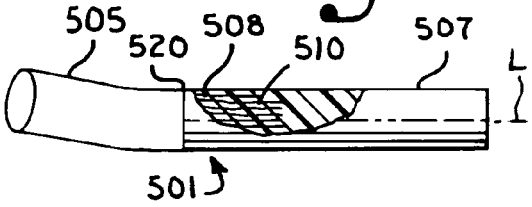
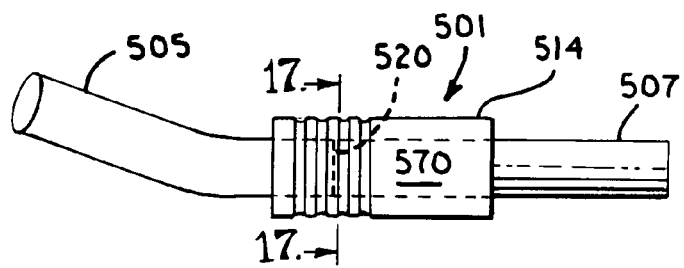
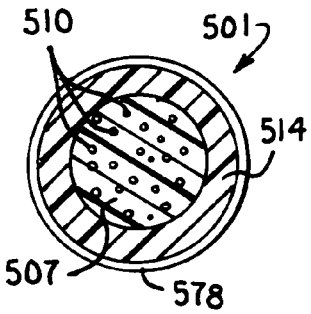
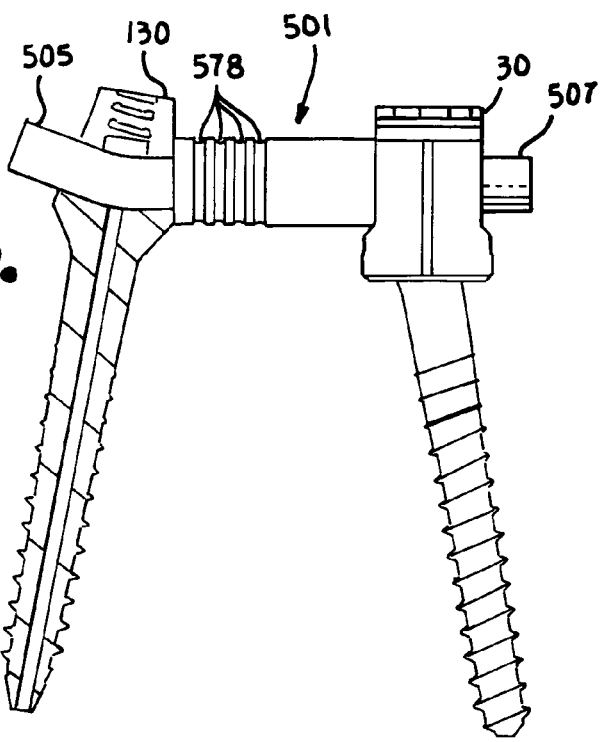

DYNAMIC STABILIZATION CONNECTING MEMBER WITH CORD CONNECTION

CROSS REFERENCE TO RELATED APPLICATIONS

This application claims the benefit of U.S. Provisional Application No. 60/922,465 filed Apr. 9, 2007; U.S. Provisional Application No. 60/898,870, filed Feb. 1, 2007; and U.S. Provisional Application No. 60/880,969, filed Jan. 18, 2007 all of which are incorporated by reference herein.

BACKGROUND OF THE INVENTION

The present invention is directed to dynamic fixation assemblies for use in bone surgery, particularly spinal surgery, and in particular to longitudinal connecting members for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

Fusion, however, has some undesirable side effects. One apparent side effect is the immobilization of a portion of the spine. Furthermore, although fusion may result in a strengthened portion of the spine, it also has been linked to more rapid degeneration due to increased stresses and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Problems may arise with such devices, however, including tissue scarring, lack of adequate spinal support and lack of fatigue strength or endurance limit. Fatigue strength has been defined as the repeated loading and unloading of a specific stress on a material structure until it fails. Fatigue strength can be tensile or distraction, compression, shear, torsion, bending, or a combination of these.

Another type of soft or dynamic system known in the art includes bone anchors connected by flexible cords or strands, typically made from a plastic material. Such a cord or strand may be threaded through cannulated spacers that are disposed between and in contact with adjacent bone anchors when such a cord or strand is implanted, tensioned and attached to or compressed against the bone anchors. The spacers typically span the distance between the bone anchors, providing limits on the bending movement of the cord or strand and thus strengthening and supporting the overall system. Such cord or strand-type systems typically require specialized bone anchors and tooling for tensioning and holding the chord or strand in the bone anchors. Thus a major disadvantage of such cord and spacer systems is their lack of interchangeability with more rigid rod systems, especially those systems that incorporate polyaxial screws as bone anchors.

The complex dynamic conditions associated with spinal movement therefore provide quite a challenge for the design of more flexible and/or elastic elongate longitudinal connecting members that exhibit an adequate fatigue strength to provide stabilization and protected motion of the spine, without fusion, and allow for some natural movement of the portion of the spine being reinforced and supported by the elongate elastic or flexible connecting member. A further challenge are situations in which a portion or length of the spine requires a more rigid stabilization, possibly including fusion with deformity correction, while another portion or length may be better supported by a more dynamic component that allows for protected movement or stress relief, especially adjacent to a long rigid rod construct. In such cases a more rigid longitudinal connecting member can be attached to a cord member of varying length.

SUMMARY OF THE INVENTION

Longitudinal connecting member assemblies according to the invention for use between at least two bone anchors provide dynamic, protected motion of the spine and may be extended to provide additional dynamic sections or more rigid support along an adjacent length of the spine, with fusion, if desired. A longitudinal connecting member assembly according to the invention includes a transition or connection portion disposed between the bone anchors, the transition portion having at least one substantially rigid portion with at least one aperture and at least one tie, such as a slender cord, extending through the aperture. In certain embodiments, first and second rigid longitudinal connecting member portions that are each attached to a bone anchor each include a plurality of apertures. Discrete ties in the form of slender cords or strands loop through the apertures of both the first and second rigid portions, providing a flexible connection therebetween. In other embodiments, ties that are integral with or otherwise attached to a larger longitudinal connecting member cord are threaded or laced through apertures in a more rigid substantially solid longitudinal connecting member, providing a flexible transition between the flexible cord that is attached to a first bone attachment structure and a rod or other shaped longitudinal member that is attached to a second adjacent bone attachment structure. In other embodiments according to the invention, ties or strands that are integral with a flexible longitudinal connecting member cord are attached to a solid molded plastic longitudinal connecting member, the ties or strands being imbedded in the connecting member, either by placement thereof within the member during a molding process or by drilling and plugging the member with the strands with application of an adhesive, thus forming a transition portion that is substantially as rigid as a remainder of the connecting member. A plastic connecting member portion for use with the invention may range in rigidity from being quite rigid (no outer sleeve required) to being flexible (requiring an outer sleeve).

Transition portions according to the invention typically further include an outer sleeve or spacer that surrounds the transition between the cord and/or ties and the rigid portion or portions, the sleeve extending between a pair of adjacent bone anchors and in contact therewith. The transition portion and the outer sleeve cooperate dynamically, both features having some flexibility, with the outer sleeve primarily protecting and limiting flexing movement of the inner transition portion. The outer sleeve may include a grooved portion that may be compressed upon installation between two bone anchors.

A variety of embodiments according to the invention are possible. For example, both a rod-to-rod transition portion and a rod-to-cord transition portion may be included in the same longitudinal connecting member. Rods or other substantially rigid structures having different measures of rigidity may be connected according to embodiments of the invention. Either rigid lengths or flexible cords may be of greater or lesser lengths for attaching to one or a plurality of bone anchors.

OBJECTS AND ADVANTAGES OF THE INVENTION

Therefore, it is an object of the present invention to overcome one or more of the problems with bone attachment assemblies described above. An object of the invention is to provide dynamic medical implant stabilization assemblies having longitudinal connecting members that include both rigid and more flexible sections or lengths, the flexible sections allowing for at least one of bending, torsion, compression and distraction of the assembly. Another object of the invention is to provide such an assembly wherein the flexible section or sections are insertable into a protective outer sleeve. A further object of the invention is to provide such an assembly wherein the outer sleeve may be compressed upon installation. A further object of the invention is to provide dynamic medical implant longitudinal connecting members that may be utilized with a variety of bone screws, hooks and other bone anchors. Another object of the invention is to provide a more rigid or solid connecting member portion or segment, if desired, such as a solid rod portion integrally linked to one or more flexible portions or segments. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a front elevational view of a dynamic fixation longitudinal connecting member according to the invention including first and second rigid rod portions and a flexible transition/connection portion.

FIG. 2 is a front elevational view of the connecting member of FIG. 1 and further including a wound cord cover.

FIG. 3 is a front elevational view of the connecting member of FIG. 2 and further including an outer sleeve.

FIG. 4 is a perspective view of the connecting member of FIG. 3 shown with a pair of cooperating bone screws.

FIG. 5 is a front elevational view of the connecting member and bone screws of FIG. 4.

FIG. 14 is an enlarged and partial front elevational view of a cord for use in a sixth embodiment of a dynamic fixation longitudinal connecting member according to the invention.

FIG. 15 is an enlarged and partial front elevational view of the cord of FIG. 14 attached to a plastic member further showing the sixth embodiment according to the invention.

FIG. 16 is an enlarged front elevational view of the sixth embodiment of a connecting member according to the invention, showing the cord and rigid member of FIG. 15 with a sleeve.

FIG. 17 is an enlarged cross-sectional view taken along the line 17-17 of FIG. 16.

FIG. 18 is an enlarged front elevational view of the connecting member of FIG. 16 shown with a pair of bone screws.

DETAILED DESCRIPTION OF THE INVENTION

Figure 6:
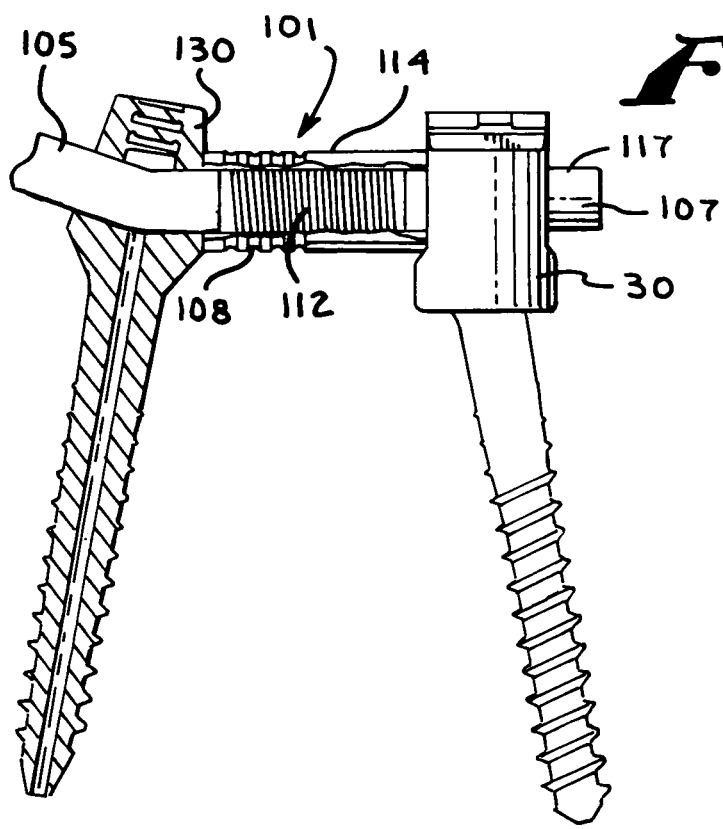
FIG. 6 is a front elevational view of a second embodiment of a dynamic fixation longitudinal connecting member according to the invention, shown with a pair of bone screws, with portions broken away to show the detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-5 and 10-12, the reference numeral 1 generally designates a non-fusion dynamic stabilization longitudinal connecting member assembly according to the present invention. The connecting member assembly 1 generally includes first and second substantially rigid members 6 and 7 with a central, dynamic connection or transition portion or segment 8 disposed therebetween. A tie or a plurality of ties 10 link the rigid members 6 and 7 at the central segment 8. The ties 10 may be any flexible elongate material that fastens, secures or unites the rigid members 6 and 7, including, but not limited to cords, threads, strings, bands, or fibers that may be single or multiple strands, including twisted, braided or plaited materials. The central segment 8 can further include an inner discrete bumper 11, a wound cover 12 and an outer sleeve or spacer 14.

Figure 12:
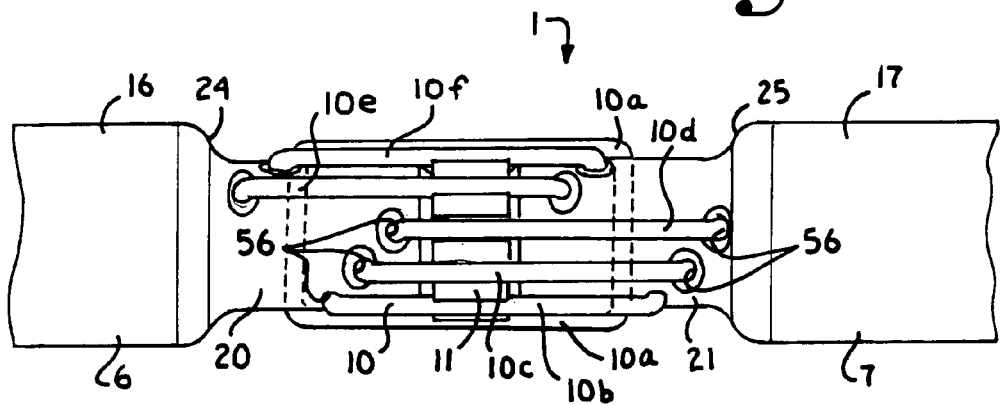
FIG. 12 is an enlarged and partial front elevational view of the connecting member of FIG. 1.

Each of the illustrated rigid members 6 and 7 are substantially cylindrical with one or more circular cross-sections along a length thereof. However, it is foreseen that the members 6 and 7 may have other forms, including but not limited to oval, square and rectangular cross-sections as well as other curved or polygonal shapes. It is foreseen that the member 6 and 7 may be of different materials, different shapes or different sizes, and thus one member may be more rigid or more flexible than the other member. The members 6 and 7 each are of a length for cooperating with at least one and up to a plurality of bone attachment members, such as bone screws or hooks. In the illustrated embodiment the rigid members 6 and 7 include respective end portions 16 and 17 of a larger diameter being integral or fixed with respective portions 20 and 21 of smaller diameter. A tapered portion 24 is disposed between the portion 16 and the portion 20. A tapered portion 25 is disposed between the portion 17 and the portion 21. In some operational embodiments, the bumper 11 may be disposed between and abut against the portions 20 and 21, as illustrated in FIG. 12. As will be described in greater detail below, the bumper 11 and the portions 20 and 21 are connected by the ties 10; the wound cord cover 12 wraps about the portions 20 and 21 and the bumper 11, forming the central connection or transition portion 8; and the connection portion 8 is received in the outer sleeve or spacer 14. The dynamic connecting member assembly 1 cooperates with at least a pair of bone anchors, such as the polyaxial bone screws, generally 30 and cooperating closure structures 32 shown in FIGS. 4 and 5, the assembly 1 being captured and fixed in place at the larger diameter rigid end portions 16 and 17 by cooperation between the bone screws 30 and the closure structures 32. The sleeve 14 can be cut to size and is shaped to closely fit between pairs of bone screws 30 or other bone anchors or implants, cooperating with the wrapped central connection portion 8 to support adjacent vertebrae.

Because the end portions 16 and 17 are substantially solid and cylindrical, the connecting member assembly 1 may be used with a wide variety of bone anchors already available for cooperation with rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The illustrated polyaxial bone screw 30 includes a shank 40 for insertion into a vertebra (not shown), the shank 40 being pivotally attached to an open receiver or head 41. The shank 40 includes a threaded outer surface and a central cannula or through-bore 42 disposed along an axis of rotation of the shank, the through-bore 42 extending between a top surface (not shown) and a bottom surface 44 of the shank 40. The bore 42 provides a passage through the shank interior for a length of wire or pin inserted into the vertebra prior to the insertion of the shank 40, the wire or pin providing a guide for insertion of the shank 40 into the vertebra.

The receiver 41 has a pair of spaced and generally parallel arms 45 that form an open generally U-shaped channel 46 therebetween that is open at distal ends of the arms 45. In the illustrated embodiment, each of the arms 45 includes a substantially cylindrical outer surface 47 disposed between a pair of substantially flat, parallel faces 48. The faces 48 are sized and shaped to engage end surfaces of the sleeve or spacer 14 as will be described in greater detail below. Each of the arms 45 also includes a radially inward or interior surface 50 having a discontinuous guide and advancement structure mateable with cooperating structure on the closure structure 32. In the illustrated embodiment, the guide and advancement structure is a partial helically wound flange form configured to mate under rotation with a similar structure on the closure structure 32. However, it is foreseen that the guide and advancement structure could alternatively be a buttress thread, a square thread, a reverse angle thread or other thread like or non-thread like helically wound advancement structures for operably guiding under rotation and advancing the closure structure 32 downward between the receiver arms 45 and having such a nature as to resist splaying of the arms 45 when the closure 32 is advanced into the U-shaped channel 46.

Each of the arms 45 also includes a V-shaped or undercut tool engagement groove 51 formed on an outer surface thereof which may be used for holding the receiver 41 with a holding tool (not shown) having projections that are received within the grooves 51 during implantation of the shank 40 into the vertebra (not shown). The grooves 51 may also cooperate with a holding tool during bone screw assembly and during subsequent installation of the connecting member assembly 1 and the closure structure 32. It is foreseen that tool receiving grooves or apertures may be configured in a variety of shapes and sizes and be disposed at other locations on the receiver arms 45.

The shank 40 and the receiver 41 may be attached in a variety of ways. For example, a spline capture connection as described in U.S. Pat. No. 6,716,214 and incorporated by reference herein, may be used. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the connecting member or may include compression members or inserts that cooperate with the bone screw shank, receiver and closure structure to secure the connecting member assembly to the bone screw and/or fix the bone screw shank at a desired angle with respect to the bone screw receiver that holds the longitudinal connecting member assembly. Furthermore, although the closure structure 32 of the present invention is illustrated with the polyaxial bone screw 30 having an open receiver or head 41, it foreseen that a variety of closure structure may be used in conjunction with any type of medical implant having an open or closed head, including monoaxial bone screws, hinged bone screws, hooks and the like used in spinal surgery.

To provide a biologically active interface with the bone, the threaded shank 40 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

The longitudinal connecting member assembly members 6 and 7 may be made from metal, metal alloys or other suitable materials, including plastic polymers such as polyetheretherketone (PEEK), ultra-high-molecular weight-polyethylene (UHMWP), polyurethanes and composites, including carbon fiber reinforced PEEK. According to the invention, the members 6 and 7 may be made from the same material or from different materials. For example, the member 6 may be made from a very rigid titanium alloy or a commercially pure titanium, while the member 7 may be made from a more flexible plastic polymer. The bumper 11 and the outer sleeve or spacer 14 may be made of a variety of materials including metals, plastics and composites. The illustrated bumper 11 and sleeve 14 are made from a plastic, such as a thermoplastic elastomer, for example, polycarbonate-urethane. In certain embodiments, in order to reduce the production of micro wear debris, the sleeve 14 inner surfaces may be coated with an ultra thin, ultra hard, ultra slick and ultra smooth coating, such as may be obtained from ion bonding techniques and/or other gas or chemical treatments.

The ties 10 and the cord that is wound about the transition or central connection portion 8 to provide the cord cover 12 may be made from a variety of materials, including polyester or other plastic fibers, strands or threads, such as polyethylene-terephthalate. Such cord and cord-like materials usually are placed under axial tension along the portion 8 during installation to facilitate a stable connecting member assembly, but typically do not illustrate elastic properties, such as any significant additional axial distraction after the assembly 1 is operatively assembled. However, it is foreseen that in some embodiments, the ties 10 and the cord cover 12 may be made of a plastic or rubber (natural or synthetic) having elastic properties, allowing for some further distraction of the central connection portion 8 at the ties 10 during operation thereof. The bumper 11 may be sized and chosen from a range of rigid to elastic materials so as to provide for a relatively more rigid assembly 1 or a relatively more flexible assembly 1 with respect to flex, bendability and/or compressibility along the central connection/transition portion 8.

Figure 11:
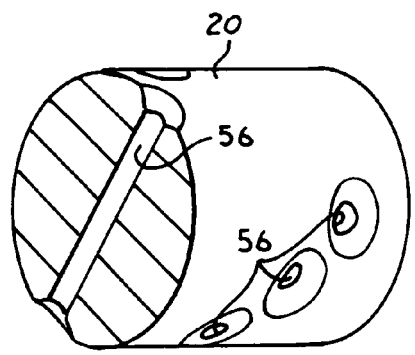
FIG. 11 is an enlarged and partial perspective view of the connecting member of FIG. 10, with portions broken away to show the detail thereof.

Returning to the longitudinal connecting member rigid members 6 and 7, the cylindrical portions 20 and 21 of the respective rigid members 6 and 7 each include a respective end surface 53 and 54 and a plurality of through apertures or bores 56, each running perpendicular to a central longitudinal axis of the member 20 or 21 as illustrated in FIG. 11. In the embodiment shown, each portion 20 and 21 has a total of six through bores 56 spaced along a length of the member running between the respective tapered portions 24, 25 and the respective end surfaces 53, 54 and disposed in a spaced helical pattern about the cylindrical portion 20, 21. In the illustrated embodiment six ties or slender cords 10 are sized and shaped for being laced through a bore 56 of each of the portions 20 and 21 and over the bumper 11 in a pattern as best shown in FIG. 12, thus making six discrete looped connections 10*a*, 10*b*, 10*c*, 10*d*, 10*e* and 10*f* between the portion 20 and the portion 21 and capturing the bumper 11 therebetween. See, for example, the loop 10*a* that is shown on either side of the portions 20 and 21 in FIG. 12 and further shown in phantom extending through the bores 56, illustrating the discrete nature of each loop. It is also foreseen that in alternative embodiments, greater or fewer than six ties or even a single tie 10 may be laced through numerous apertures in the portions 20 and 21 to connect the portion 20 with the portion 21. In the illustrated embodiment, ends of each of the elongate ties 10 are knotted, fused or otherwise secured to provide each discrete loop 10*a*, 10*b*, 10*c*, 10*d*, 10*e* and 10*f*.

Figure 10:
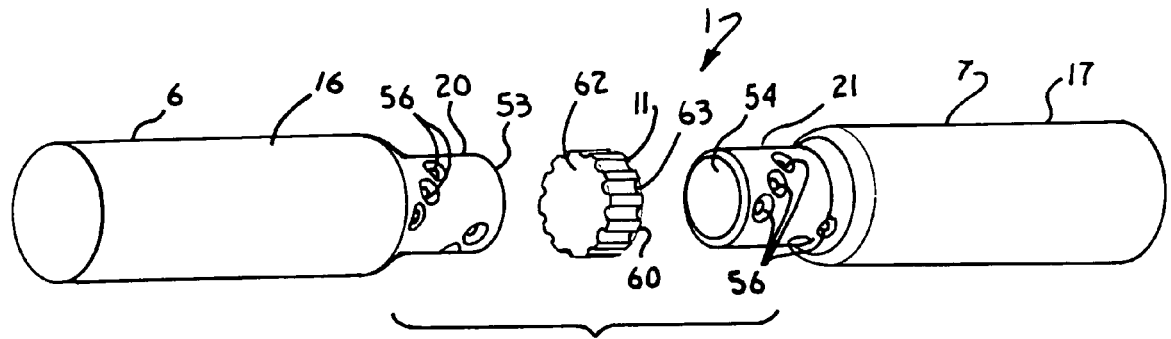
FIG. 10 is an enlarged perspective and exploded view of the connecting member of FIG. 1, shown without the connecting ties.

As illustrated in FIG. 10, the bumper 11 is substantially cylindrical and includes outer grooves 60 sized and shaped to receive the ties 10 and thereby provide a channel for each tie 10 to aid in a uniform alignment of the tie 10 between the portions 20 and 21. The bumper 11 further includes substantially planar opposed front and back surfaces 62 and 63 for contact with respective surfaces 53 and 54 of the portions 20 and 21.

As illustrated in FIG. 2, the cord cover 12 is also a strand or cord that is wrapped about the portions 20 and 21 and the bumper 11 and then secured thereto by tying, fusing or otherwise fixing. The cord cover 12 may be made out of a variety of materials, including polyester fiber. When the mid portion 8 formed by the portions 20 and 21, bumper 11, the ties 10 and the cord cover 12 is fixed to bone screws 30 by engagement of the end portions 16 and 17 with such screws, the tie-connected mid-portion 8 in combination with the sleeve 14 provides relief (e.g., shock absorption) and limited movement with respect to flexion, extension, torsion, distraction and compressive forces placed on the assembly 1.

With particular reference to FIG. 3, the sleeve or spacer 14 advantageously cooperates with the corded 12 central connection or transition portion 8, providing limitation and protection of movement of the portion 8. The sleeve 14 also protects patient body tissue from damage that might otherwise occur in the vicinity of the corded central portion 8. Thus, the sleeve 14 is sized and shaped for substantially even and precise alignment and substantial contact between flat end faces 68 and 69 of the sleeve 14 and cooperating flat side surfaces 48 of the receivers 41. Furthermore, as will be discussed in greater detail below, in certain embodiments according to the invention, when the sleeve 14 is implanted, and the closure structures 32 are tightened, the tools utilized to implant the assembly 1 and/or the bone screws 30 may be manipulated so as to axially compress the sleeve 14, now substantially coaxial with the central connection portion 8 axis A, between facing surfaces 48 of adjacent receivers 41. In some embodiments, such compression during installation results in some additional tension and/or distraction of the ties 10 of the central connection portion 8 when the implantation tools are removed from the bone screws 30, as the sleeve surfaces 68 and 69 then press against the facing bone screw surfaces 48, but the connection portion 8 is otherwise fixed with respect to each of the bone screws 30 as the portions 16 and 17 are each fixedly captured within a receiver channel 46.

Such dynamic tension/compression relationship between the sleeve 14 and the central connection portion 8 provides further strength and stability to the overall assembly.

The illustrated sleeve 14 is substantially cylindrical with an external substantially cylindrical surface 70 and an internal substantially cylindrical and smooth surface 72 defining a bore with a circular cross section extending through the sleeve 14. It is foreseen that in some embodiments, the sleeve may be of square, rectangular or other cross-section including curved or polygonal shapes. In the illustrated embodiment, the sleeve 14 further includes a plurality of compression grooves 78. Sleeves according to the invention may include one, none or any desired number of grooves 78. Each of the illustrated grooves 78 is substantially uniform and circular in cross-section, being formed in the external surface 70 and extending radially toward the internal surface 72. The internal surface 72 is of a slightly greater diameter than a substantially cylindrical outer diameter formed by the cover 12 that wraps about the central connection portion 8. The cord cover 12 outer surface is substantially flush with the larger diameter portions 16 and 17, resulting in a connecting member with an overall substantially uniform outer diameter. The size of the internal surface 72 allows for axially directed sliding movement of the sleeve 14 with respect to the end portions 16 and 17 and the central portion 8. When the sleeve 14 is received about the central connection portion 8, the sleeve 14 completely surrounds the central portion 8 as illustrated in FIG. 3. It is noted that in addition to limiting the bendability of the central connection portion 8 and thus providing strength and stability to the assembly 1, the sleeve 14 also keeps scar tissue from growing into the portion 8 through the wound cord cover 12, thus eliminating the need for a sheath-like structure to be placed, adhered or otherwise applied to the cord cover 12 on the central connection portion 8.

With reference to FIG. 4, the closure structure 32 can be any of a variety of different types of closure structures for use in conjunction with the present invention with suitable mating structure on the interior surface 50 of the upstanding arms 45 of the receiver 41. The illustrated closure structure 32 is rotatable between the spaced arms 45, but could be a slide-in closure structure. The illustrated closure structure 32 is substantially cylindrical and includes an outer helically wound guide and advancement structure in the form of a flange form that operably joins with the guide and advancement structure disposed on the interior 50 of the arms 45. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 32 downward between the arms 45 and having such a nature as to resist splaying of the arms 45 when the closure structure 32 is advanced into the U-shaped channel 46. The illustrated closure structure 32 also includes a top surface with an internal drive in the form of an aperture 80 that may be a hex drive, a star-shaped internal drive, for example, sold under the trademark TORX or other internal drives such as slotted, tri-wing, spanner, two or more apertures of various shapes, and the like. A driving tool (not shown) sized and shaped for engagement with the internal drive 80 is used for both rotatable engagement and, if needed, disengagement of the closure 32 from the arms 45. It is also foreseen that the closure structure 32 may alternatively include a break-off head designed to allow such a head to break from a base of the closure at a preselected torque, for example, 70 to 140 inch pounds. Such a closure structure would also include a base having an internal drive to be used for closure removal.

In use, at least two bone screws 30 are implanted into vertebrae for use with the longitudinal connecting member assembly 1. Each vertebra may be pre-drilled to minimize stressing the bone. Furthermore, when a cannulated bone screw shank is utilized, each vertebra will have a guide wire or pin (not shown) inserted therein that is shaped for the bone screw cannula 42 of the bone screw shank 40 and provides a guide for the placement and angle of the shank 40 with respect to the cooperating vertebra. A further tap hole may be made and the shank 40 is then driven into the vertebra by rotation of a driving tool (not shown) that engages a driving feature on or near a top portion of the shank 40. It is foreseen that the screws 30 and the longitudinal connecting member assembly 1 can be inserted in a percutaneous or minimally invasive surgical manner.

With particular reference to FIGS. 2-3, the longitudinal connecting member assembly 1 that has been factory assembled to include the bumper 11, looped ties 10 and the cord cover 12 is assembled with the sleeve 14 by inserting either the end portion 16 or end portion 17 into the bore defined by the inner cylindrical surface 72 of the outer sleeve 14. The sleeve 14 is moved into position over the central portion 8 and between the end portions 16 and 17, thus covering or encompassing the cord cover 12.

The connecting member assembly 1 is eventually positioned in an open or percutaneous manner in cooperation with the at least two bone screws 30 with the sleeve 14 disposed between the two bone screws 30 and the end portions 16 and 17 each within the U-shaped channels 46 of the two bone screws 30. A closure structure 32 is then inserted into and advanced between the arms 45 of each of the bone screws 30. The closure structure 32 is rotated, using a tool engaged with the inner drive 80 until a selected pressure is reached at which point the end portion 16 or 17 is urged toward, but not completely seated in the channel 46. For example, about 80 to about 120 inch pounds pressure may be required for fixing the bone screw shank 40 with respect to the receiver 41. Downward movement of the closure structure 32 into the channel 46 presses a respective end portion 16 or 17 downward into engagement with a top or other upper portion of the respective bone screw shank 40, pressing a respective retaining structure (not shown) or shank head portion into engagement with the respective receiver 41, thus setting an angle of articulation of the respective shank 40 with respect to the respective receiver 41, clamping the shank 40 into a fixed position with respect to the receiver 41. The receiver 41, the shank 40 and the retaining structure cooperate in such a manner that the receiver 41 and the shank 40 can be secured at any of a plurality of angles, articulations or rotational alignments relative to one another and within a selected range of angles both from side to side and from front to rear, to enable flexible or articulated engagement of the receiver 41 with the shank 40 until both are locked or fixed relative to each other.

Alternatively, it is foreseen that the capture of the connecting member assembly 1 by bone screws or other bone anchors and cooperating closure structures could further involve the use of an upper and/or a lower compression member or insert disposed within the receiver 41. Furthermore, the assembly 1 may cooperate with an open receiver that is integral or fixed in position with respect to a bone screw shank or bone hook, or with a receiver having limited angular movement with respect to the shank, such as a hinged connection, also with or without other compression members or inserts for fixing the assembly 1, the receiver and/or the bone anchor in a desired position or orientation with respect to the cooperating vertebrae.

Prior to final tightening of the closure structures 32 the members 6 and 7 may be pulled away from one another to place the central connection portion 8 in tension. Also, in certain embodiments, as the closure structures 32 are rotated and then tightened against the end portions 16 and 17 within a pair of spaced bone screws 30, the bone screws 30 may be tilted or otherwise pressed toward one another, thereby compressing the sleeve 14. When the insertion and tightening tools are removed, the sleeve 14, pressing against facing surfaces 48 of the cooperating bone screw receivers 41, placing additional axial tension upon ties 10 and the cord cover 12 of the central connection portion 8. The assembly 1 is thus substantially dynamically loaded and oriented relative to the cooperating vertebra, providing stress relief (e.g., some shock absorption) and protected movement with respect to flexing and compressive forces (and in certain embodiments, if elastic ties and cord cover are utilized, also distractive forces) placed on the assembly 1 and the two connected bone screws 30. The ties 10 and the bumper 11 also allow the central portion 8 to twist or turn, providing relief for torsional stresses. The sleeve 14 limits such torsional movement as well as bending movement of the central connection portion 8, providing spinal support.

If removal of the assembly 1 from any of the bone screw assemblies 30 is necessary, or if it is desired to release the assembly 1 at a particular location, disassembly is accomplished by using the driving tool (not shown) that mates with the internal drive 80 on the closure structure 32 to rotate and remove the closure structure 32 from the receiver 41. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the end portions 16 and 17, utilizing the same receivers 41 and closure structures 32. Furthermore, it is noted that the end portion 16 and/or 17 may be elongate, allowing for connection of a rigid rod portion or portions of the assembly 1 with additional bone screws or other bone anchors along a patient's spine.

Figure 13:
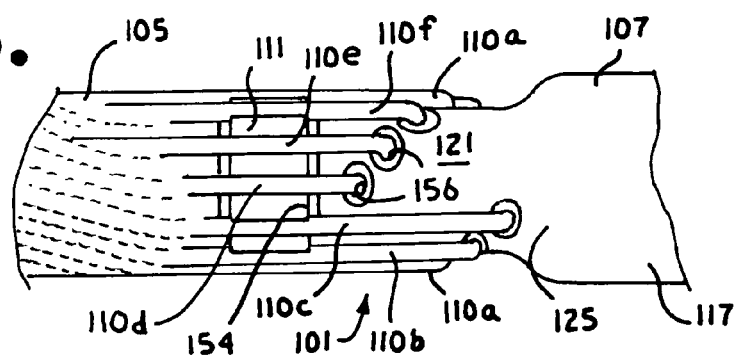
FIG. 13 is an enlarged and partial front elevational view of the connecting member of FIG. 6.

With particular reference to FIGS. 6 and 13, an alternative longitudinal connecting member assembly embodiment according to the invention, generally 101 includes a flexible cord or cable 105 attached to a rigid member 107 that is identical or substantially similar to the member 7 previously described herein. The cord 105 is both flexible and strong and may be made from a variety of materials including but not limited to polyester fibers that are twisted, plaited, bonded or otherwise connected to result in a strong cord or rope. The cord 105 is sized and shaped to be received in a bone screw or other bone anchor 130. The cord 105 may be of a polyethylene material as is known in the art for use with cannulated spacers and cooperating bone anchors. Such a cord typically extends or stretches somewhat but exhibits little further elasticity after being tensioned during implantation.

The member 107 includes a larger diameter portion 117 receivable in the bone anchor 30 previously described herein, a smaller diameter portion 121, a tapered portion 125, an end surface 154 and through bores 156 spaced in a helical pattern, all of which are identical or substantially similar to the larger diameter portion 17, smaller diameter portion 21, tapered portion 25, end surface 54 and spaced through bores 56 of the rigid member 7 previously described herein with respect to the assembly 1. Similar to the assembly 1, the assembly 101 has a central connection portion 108 that includes the smaller diameter portion 121 and further includes a bumper 111, ties 110, a cord cover 112 and an outer sleeve 114 identical or substantially similar to the respective bumper 11, ties 10, cord cover 12 and sleeve 14 of the assembly 1 previously described herein. The individual ties 110 are threaded through, integral or integrally woven into the larger cord or cable 105 and then form discrete loops 110a, 110b, 110c, 110d, 110e and 110f that pass through the bores 156 in the portion 121 of the member 107 in a manner substantially similar to the cord loops 10a, 10b, 10c, 10d, 10e and 10f extending through the portion 21 of the member 7 of the assembly 1.

The assembly 101 is shown attached to a bone screw 30 previously described herein at the end portion 117 and to the fixed, closed bone screw 130 at the flexible cord portion 105. For example, suitable hinged and fixed bone screws for mating with the cord 105 are described in Applicant's U.S. patent application Ser. No. 11/328,481 filed Jan. 9, 2006, Publication No. 20060111715, incorporated by reference herein. Although not shown, both the illustrated polyaxial and fixed bone screws each include a closure structure with a helically wound guide and advancement structure for mating engagement with the particular bone screw. Since the bone screw 130 is of a closed, fixed construction the mating closure structure (not shown) is a set screw. Furthermore, in order to securely fix the cord 105 in place, the set screw may include points or other protruding structures and/or a compression or holding member or insert may desirably be placed between the cord 105 and the set screw or other closure structure.

As with the assembly 1, the assembly 101 readily cooperates with a wide variety of bone anchors and closures, also as previously described herein at the rigid portion 107 and further cooperates with a variety of bone anchors adapted for use with cords at the portion 105, and thus is not limited in use to the particular bone screws disclosed herein.

In use, the longitudinal connecting member assembly 101 is factory assembled to provide the flexible central transition portion 108 that includes the bumper 111 captured between the section 121 and the cord 105 by the looped ties 110 as illustrated in FIG. 13 and further protected by the cord cover 112 as shown in FIG. 6. The sleeve 114 is slidable onto both the rigid portion 107 and the corded portion 105, and placable about the cord covered central or transition portion 108, also as shown in FIG. 6. The sleeve 114 (as well as the sleeve 14 previously described herein) may be cut to the precise desired size by the surgeon. The connecting member assembly 101 is eventually positioned in an open or percutaneous manner in cooperation with the bone screws 30 and 130 with the sleeve 114 disposed between the two bone screws 30 and fitting closely therebetween. The corded portion 105 is tensioned during installation. As with the assembly 1, in certain embodiments according to the invention, when the closure structures are inserted into the bone screws, the sleeve 114 may be compressed by moving the bone screws 30 and 130 toward one another during tightening of the closure structures within the bone screw receivers. When the insertion and tightening tools are removed, the sleeve 114, pressing against facing surfaces of the adjacent cooperating bone screw receivers places additional tension on the ties 110 of the central connection portion 108. The assembly 101 is thus substantially dynamically loaded and oriented relative to the cooperating vertebra. The ties 110 and the bumper 111 also allow the central portion 108 to compress and twist or turn, providing relief for torsional stresses. The sleeve 114 limits such torsional movement as well as bending movement of the central connection/transition portion 108, providing spinal support. Furthermore, if the sleeve 114 is compressed during installation, the sleeve may extend slightly in response to body motion and/or flexion of the transition portion 108, for example.

Figure 7:
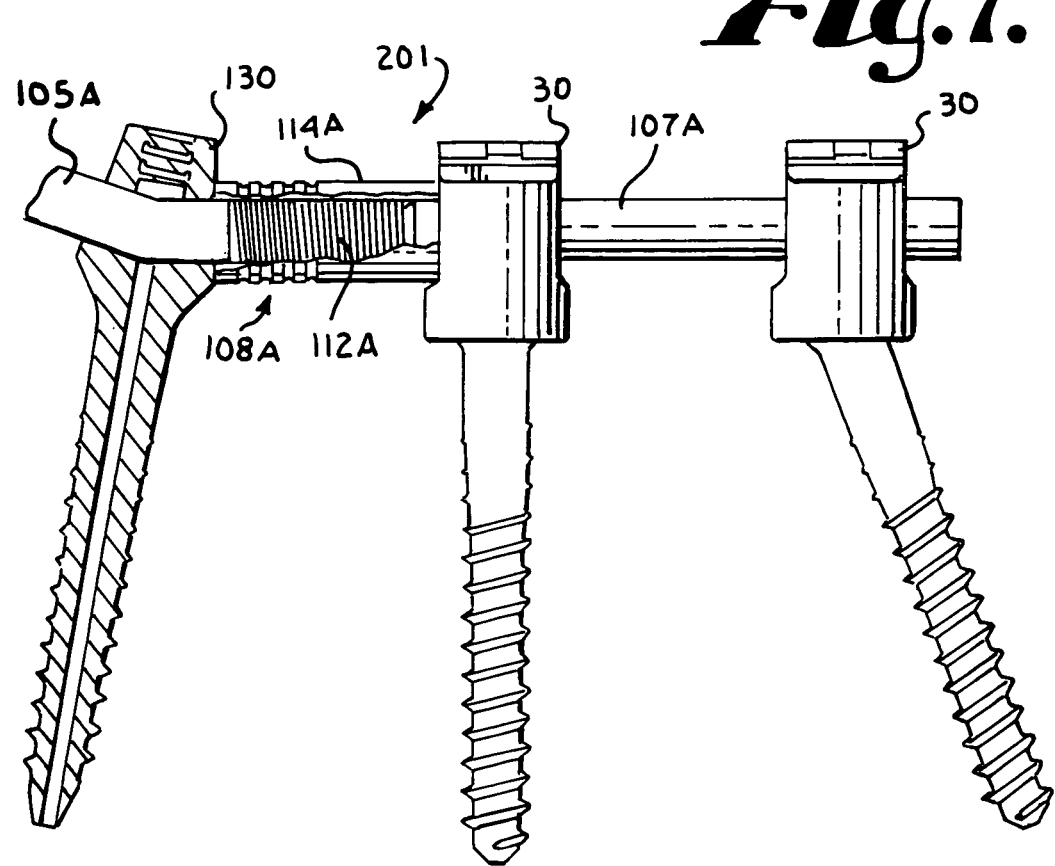
FIG. 7 is a front elevational view of a third embodiment of a dynamic fixation longitudinal connecting member according to the invention, shown with three bone screws, with portions broken away to show the detail thereof.
Figure 8:
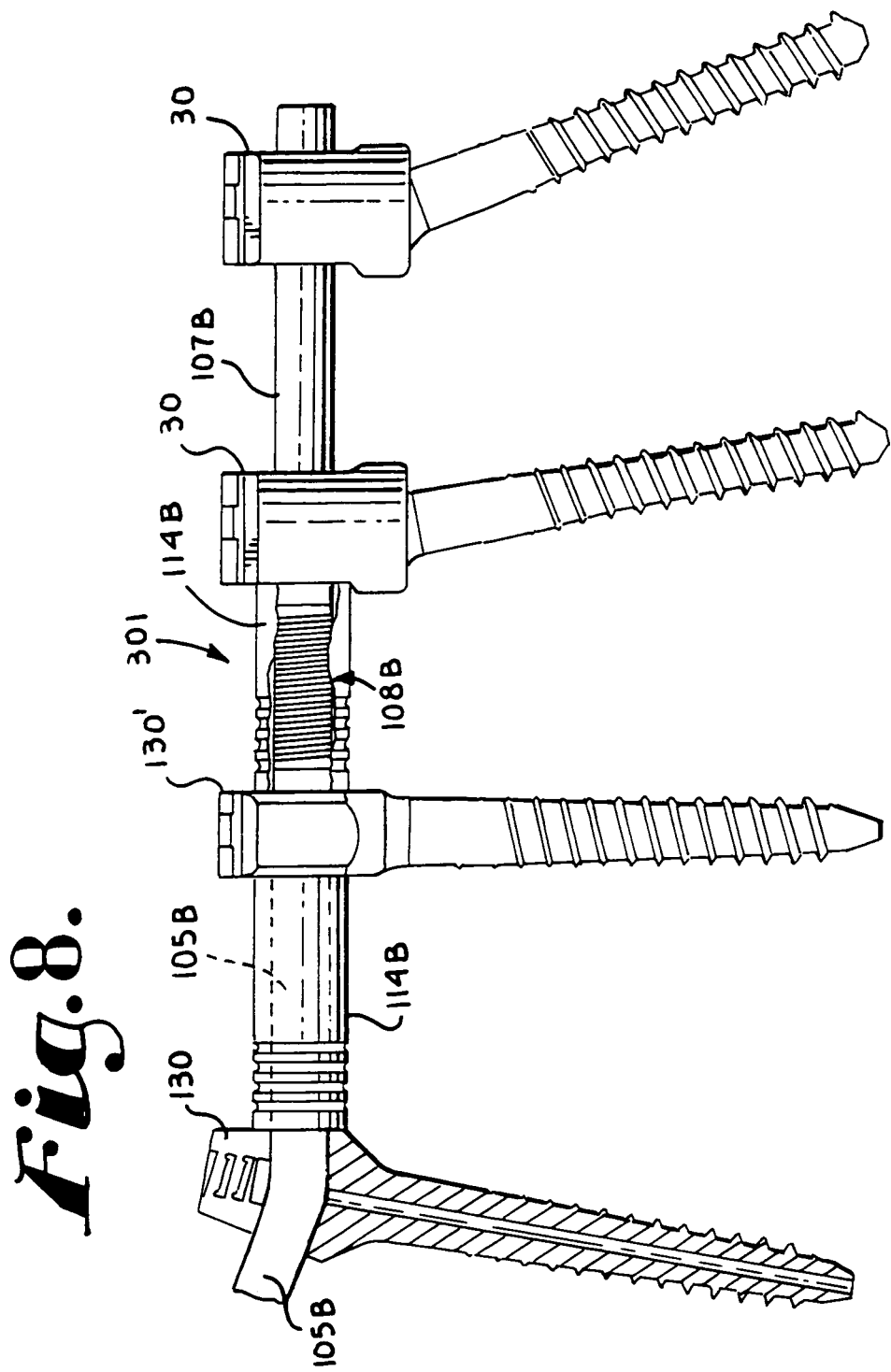
FIG. 8 is a front elevational view of a fourth embodiment of a dynamic fixation longitudinal connecting member according to the invention, shown with four bone screws, with portions broken away to show the detail thereof.
Figure 9:
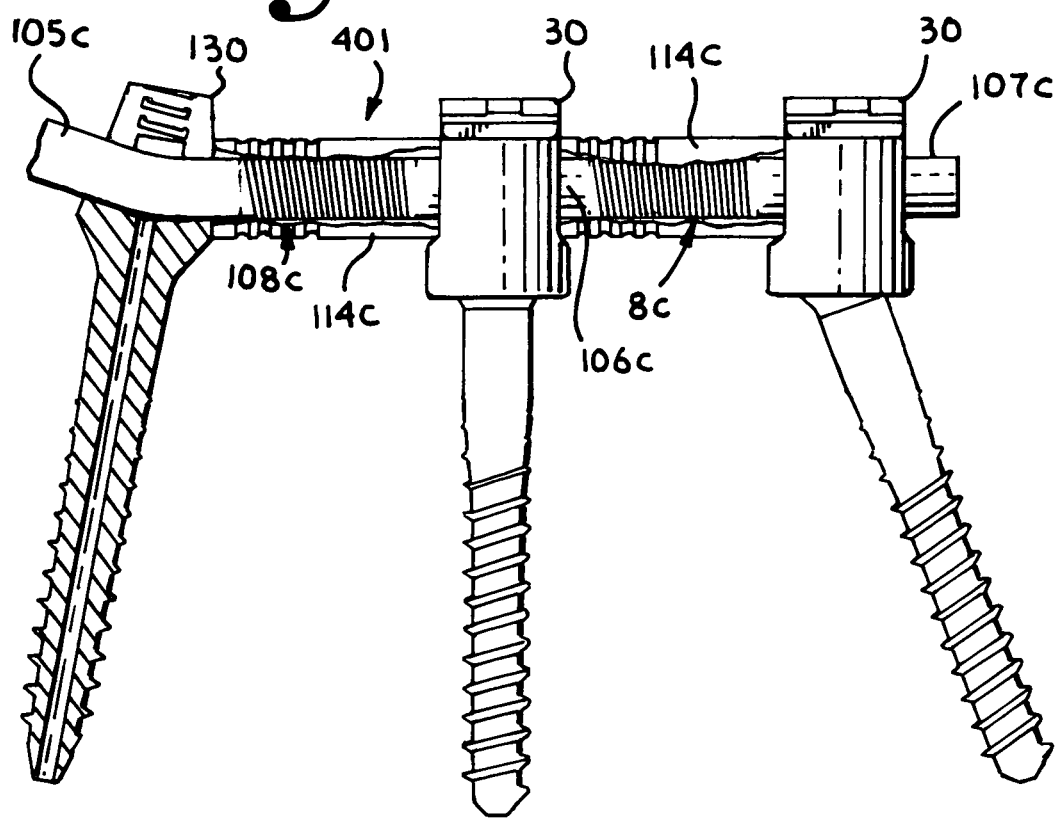
FIG. 9 is a front elevational view of a fifth embodiment of a dynamic fixation longitudinal connecting member according to the invention, shown with three bone screws, with portions broken away to show the detail thereof.

With reference to FIGS. 7, 8 and 9, dynamic longitudinal connecting members according to the invention may include rigid rod portions, flexible cords and flexible cord/rod transition portions in a variety of combinations as desired to provide both rigid and/or various levels of dynamic support of a patient's spine. For example, a third embodiment according to the invention shown in FIG. 7 and generally designated 201 includes a transition portion or segment 108A substantially identical to the portion 108 previously described herein and shown in FIG. 6. However a rigid rod portion 107A is of a longer length than the rigid portion 107 shown in FIG. 6, the rigid portion 107A sized to be received in two bone screws 30.

With reference to FIG. 8, a fourth embodiment according to the invention, generally 301 includes a central connection or transition portion 108B identical or substantially similar to the portion 108 previously described herein and shown in FIGS. 6 and 13. However, the longitudinal connecting member 301 includes an extended cord portion 105B and an extended rigid portion 107B. The connecting member 301 is thus sized and shaped to attach to at least four bone screws: illustrated herein as two polyaxial screws 30 at the portion 107B, a fixed or monoaxial closed bone screw 130 and a fixed open bone screw 130' at the cord 105B. Thus, the member 301 provides an extended length of flexible dynamic stabilization at the transition 108B and the cord 105B as well as extended rigid support along the rigid length 107B. Two sleeves 114B that are identical or substantially similar to the sleeve 14 previously described herein are included in the embodiment 301: one between the screw 130 and the screw 130' and the other between the screw 130' and the polyaxial screw 30. It is further noted that the rigid portion 107B may be straight or curved, pre-bent or curvilinear.

With reference to FIG. 9, another alternative longitudinal connecting member assembly according to the invention, generally 401 includes a connection or transition portion 8C identical or substantially similar to the portion 8 previously described herein and shown in FIGS. 1-5 and 12 and also a connection or transition portion 108C identical or substantially similar to the portion 108 previously described herein and shown in FIG. 6. Thus, the connecting member 401 includes a cord 105C similar to the cord 105 of the connecting member 1 and also end portions 106C and 107C similar to respective portions 6 and 7 of the connecting member 1. The connecting member 401 is thus sized and shaped to attach to at least three bone screws: two polyaxial screws 30 at the portions 106C and 107C; and a fixed or monoaxial closed bone screw 130 at the cord 105C. Thus there is provided a flexible dynamic stabilization along the entire connecting member 401, with both of the transition portions 8C and 108C being surrounded and protected by sleeves 114C that are identical or substantially similar to the sleeve 14 previously described herein with respect to the connecting member 1.

With reference to FIGS. 14-18 another alternative longitudinal connecting member assembly according to the invention, generally 501 includes a flexible cord or cable 505 attached to a molded plastic member 507 that may be rigid or have some flexibility, depending upon the material used to fabricate the member 507. The cord 505 is identical or substantially similar to the cord 105 previously described herein with respect to the connecting member assembly 101 and is shown in FIG. 18 received within the closed fixed bone screw 130 previously described herein. Near an end 508 thereof, the cord 505 includes smaller diameter elongate ties, strands or fibers 510 that are integral, integrally woven, or otherwise fixed to the cord 505. The cord 505 and the plastic member 507 may be fixedly attached to one another in a variety of ways. In one embodiment according to the invention, small apertures or holes are drilled in the plastic member 507 at or near the end 520. Such apertures may be drilled parallel to a longitudinal axis L of the plastic member 507 or at an angle thereto, such as an angle oblique to the longitudinal axis L. The strands 510 are then inserted or plugged into the apertures in the plastic member 507 and adhered to the plastic member 507 with an adhesive and/or heat. The adhesive may be applied before, during or after plugging of the apertures with the strands 510, with both the adhesive and the strands 510 extending into and penetrating the member 507 at the drilled apertures.

Also with reference to FIGS. 14-18, alternatively, the strands 510 are embedded into the member 507 during a fabrication process wherein the member 507 is molded adjacent to the cord 505 with the strands 510 being molded within the molded plastic of the member 507. Thus, during fabrication, the plastic flows in and around and bonds to the individual strands or fibers 510, resulting in a single or discrete longitudinal connecting member 501 both a corded portion and a solid cylindrical portion. It is believed that certain process parameters, such as performing the molding process in a vacuum, further aids in the adhesion or bonding of the plastic material to the strands or fibers 510. Longitudinal connecting members according to the invention may include one or more corded or molded sections along a length thereof. Molded sections made from different materials may be included along a length of a connecting member with corded sections disposed therebetween.

With particular reference to FIGS. 15 and 17, the illustrated molded member 507 is in the form of a cylindrical rod that includes the end 520 that is disposed near or approximately at the end 508 of the cord such that all of the strands or fibers 510 are substantially imbedded or adhered within the molded member 507. The molded member 507 may be made from a variety of rigid or flexible plastics, including but not limited to plastic polymers such as polyetheretherketone (PEEK), ultra-high-molecular weight-polyethylene (UHMWP), polyurethanes and composites. It is foreseen that in certain embodiments according to the invention, the molded member may include elastomeric materials, such as natural or synthetic elastomers, including, but not limited to polyisoprene (natural rubber), and synthetic polymers, copolymers, and thermoplastic elastomers, and mixtures thereof. Although illustrated as a solid rod with a circular cross-section, the member 507 may have other forms, including but not limited to oval, square and rectangular cross-sections as well as other curved or polygonal shapes of various sizes.

The assembly 501 further includes a sleeve or spacer 514 having an outer cylindrical surface 570 and a plurality of grooves 578. The sleeve 501 is identical or substantially similar to the sleeves 14 and 114 previously described herein with respect to the respective assemblies 1 and 101. The sleeve 514 receives either the cord 505 or the molded member 507 and is eventually operatively positioned over the end 520 that is the juncture between the cord 505 of the molded member 507. In order to have low or no wear debris, the sleeve 514 inner surfaces and/or outer surfaces of a cooperating portion of the member 507 may be coated with an ultra thin, ultra hard, ultra slick and ultra smooth coating, such as may be obtained from ion bonding techniques and/or other gas or chemical treatments. It is foreseen that the member 507 may be sized and made from such materials as to provide for a relatively more rigid assembly 501 or a relatively more flexible assembly 501 with respect to flex or bendability along the portion 507.

When the portion 505 is elongate, sleeves 514 are disposed between bone screws along such length. Furthermore, if the member 507 is flexible, sleeves 514 are preferably disposed between bone screws along the member 507 length. Also, since the distance between the bone screws can vary, the member 507 may need to be more or less stiff.

The assembly 501 is shown attached to a bone screw 30 previously described herein at the member 507 and to the fixed, closed bone screw 130 previously described herein at the flexible cord portion 505. As with the cord portion 105 previously described herein, suitable hinged and fixed bone screws for mating with the cord 505 are described in Applicant's U.S. patent application Ser. No. 11/328,481 filed Jan. 9, 2006, Publication No. 20060111715, incorporated by reference herein. Although not shown, both the illustrated polyaxial and fixed bone screws each include a closure structure with a helically wound guide and advancement structure for mating engagement with the particular bone screw. Since the bone screw 130 is of a closed, fixed construction the mating closure structure (not shown) is a set screw. Furthermore, in order to securely fix the cord 505 in place, the set screw may include points or other protruding structures and/or a compression or holding member or insert may desirably be placed between the cord 505 and the set screw or other closure structure.

As with the assemblies 1 and 101 previously described herein, the assembly 501 readily cooperates with a wide variety of bone anchors and closures, also as previously described herein at the solid molded portion or member 507 and further cooperates with a variety of bone anchors adapted for use with cords at the member 505, and thus is not limited in use to the particular bone screws disclosed herein.

In use, the longitudinal connecting member assembly 501 is factory fabricated by a molding and/or machining and bonding process to provide a singular longitudinal connecting member having the corded member or portion 505 and a solid molded member or portion 507. The sleeve 514 is cut to the precise desired size by the surgeon for fitting closely between the bone screws 30 and 130. The sleeve 514 is then slid onto either the molded member 507 or the corded portion 505, and placed about the connecting member 501 at the transition portion indicated by the end 520 of the molded member 507 as shown in FIG. 16. The connecting member assembly 501 is eventually positioned in an open or percutaneous manner in cooperation with the bone screws 30 and 130 with the sleeve 514 disposed between the two bone screws 30 and fitting closely therebetween. The corded portion 505 disposed between the bone screw 130 and the molded member 507 is typically tensioned during installation. As with the assembly 1, in certain embodiments according to the invention, when the closure structures are inserted into the bone screws, the sleeve 514 may be compressed by moving the bone screws 30 and 130 toward one another during tightening of the closure structures within the bone screw receivers. In such embodiments, for example, when the molded member 507 has some elastomeric properties, when the insertion and tightening tools are removed, the sleeve 514, pressing against facing surfaces of the adjacent cooperating bone screw receivers places additional tension upon the cord 505 and molded member 507 that make up a transition portion that is disposed between the two bone screws 30 and 130. The assembly 501 is thus substantially dynamically loaded and oriented relative to the cooperating vertebra. The sleeve 514 limits torsional movement as well as bending movement of the cord/rod transition portion that is disposed between the bone screws 30 and 130, providing spinal support. Furthermore, if the sleeve 514 is compressed during installation, the sleeve may extend during body motion (with possible simultaneous distraction of the transition portion if the member 507 includes an elastomeric material).

If removal of the assembly 501 from any of the bone screw assemblies 30 or 130 is necessary, or if it is desired to release the assembly 501 at a particular location, disassembly is accomplished by using the driving tool (not shown) that mates with the internal drives of the cooperating closure structures or set screws to rotate and remove such closure structure or set screw from the bone screws 30 or 130. Disassembly is then accomplished in reverse order to the procedure described previously herein for assembly.

It is to be understood that while certain forms of the present invention have been illustrated and described herein, it is not to be limited to the specific forms or arrangement of parts described and shown.

What is claimed and desired to be secured by Letters Patent is as follows:

1. In a medical spinal implant assembly having at least two bone anchors cooperating with a longitudinal connecting member, the improvement wherein the connecting member comprises:
   a) a substantially stiff connecting member portion secured to a first of the at least two bone anchors;
   b) a soft connecting member portion extending through a second of the at least two bone anchors, the soft member having an end; the soft connecting member portion being elastic and under pre-tension when the connecting member is joined to the bone anchors;
   c) a transition portion at least partially disposed between the at least two bone anchors, the transition portion comprising a connection of the soft member end to the stiff connecting member portion; and
   d) an outer compressible sleeve member disposed between the at least two bone anchors and having overlapping engagement with the transition portion to stabilize a spinal motion segment of the spine when under compression; wherein
   e) the soft connecting member portion, when under tension due to the pre-tensioning thereof, cooperates with the second bone anchor so as to operably stabilize the spinal motion segment of the spine and cause compression of the outer sleeve member.

2. The improvement of claim 1 wherein the stiff connecting member portion is substantially solid.

3. The improvement of claim 1 wherein the soft connecting member portion is a tensioned cord.

4. The improvement of claim 3 wherein the stiff connecting member portion is made from plastic and at least one soft flexible tie member of the tensioned cord penetrates the plastic.

5. The improvement of claim 4 wherein the at least one soft flexible tie member is bonded to the stiff connecting member with an adhesive.

6. The improvement of claim 3 wherein the cord and stiff connecting member have substantially the same diameter prior to tensioning.

7. The improvement of claim 1 wherein the stiff connecting member portion is a substantially rigid rod.

8. The improvement of claim 1 wherein the stiff connecting member portion is an elongate rod.

9. The improvement of claim 1 wherein the stiff connecting member portion is made of a metal and the soft member is made of a non-metal.

10. In a medical implant assembly having at least two bone attachment structures cooperating with a longitudinal connecting member, the improvement wherein the connecting member comprises:
   a) the connecting member includes an elastic portion under pre-tension between the bone attachment structures; and
   b) a transition portion at least partially disposed between the at least two bone attachment structures, the transition portion joining a rigid portion to the elastic portion and having
      i) at least one aperture approximate at least one end of the rigid portion; and
      ii) at least one elongate tensionable cord member positioned within the aperture and fixed thereto; wherein
      iii) a compressible outer sleeve engages the transition portion to hold the outer sleeve in compression when the elastic portion is in tension.

11. The improvement of claim 10 wherein the at least one substantially rigid portion is a first rigid portion having at least a first aperture and further comprising a second rigid portion having at least a second aperture, the at least one cord member being a tie extending through both the first and second apertures.

12. The improvement of claim 11 wherein both the first and second rigid portions are each elongate rods.

13. The improvement of claim 10 wherein the at least one tensionable cord member is flexible and sized and shaped so as to be securable to one of the bone attachment structures, the cord member thereby connecting the bone attachment structure to the rigid portion through the transition portion after tensioning and securing the cord member to the bone attachment structure.

14. The improvement of claim 13 comprising a plurality of cord members attached to a flexible cord, each cord member extending through an aperture of the rigid portion.

15. The improvement of claim 10 wherein the rigid portion has a plurality of apertures and further comprising a plurality of cord members, each cord member extending through an aperture.

16. The improvement of claim 10 further comprising the outer sleeve having a bore and at least partially covering the transition portion, the outer sleeve holding the cord member in tension when the outer sleeve is compressively engaged.

17. The improvement of claim 16 wherein the outer sleeve extends between and has ends facing the at least two bone attachment structures.

18. The improvement of claim 17 wherein the outer sleeve is compressively deformed during installation.

19. The improvement of claim 17 wherein the outer sleeve has at least one groove formed in an outer surface.

20. The improvement of claim 16 wherein
   a) the outer sleeve extends between at least two bone attachment structures, wherein at least one of the bone attachment structures has an open U-shaped channel.

21. The improvement of claim 10 wherein the cord is tensioned.

22. In a medical spinal implant assembly having at least first, second and third bone anchors cooperating with a longitudinal connecting member, the improvement wherein the connecting member comprises:
   a) a substantially stiff connecting member having a first portion with a first width, the first portion being secured to the first bone anchor; and
   b) a tensionable and elastic soft connecting member attached to the stiff connecting member and being under pre-tension when the connecting member is joined to the bone anchors, the soft connecting member having a second portion at least partially surrounded by an outer sleeve member, the outer sleeve member being positioned between the second and third bone anchors so as to operably stabilize a segment of the spine, wherein the outer sleeve member is compressed and the soft member is tensioned; wherein
   c) the soft connecting member second portion is positioned within the third bone anchor, the second portion having a second width not greater than the first width of the first portion of the stiff connecting member, the second portion cooperating with the third bone anchor to hold the soft connecting member in tension.

23. The improvement of claim 22 wherein
   a) the stiff connecting member is substantially solid.

24. The improvement of claim 23 wherein
   a) the stiff connecting member is made from plastic and at least one flexible tie penetrates the plastic.

25. The improvement of claim 24 wherein
   a) the at least one flexible tie is bonded to the stiff connecting member with an adhesive.

26. The improvement of claim 22 wherein
   a) the soft connecting member is a cord.

27. The improvement of claim 22 wherein
   a) the soft connecting member extends into an opening in the stiff connecting member.

28. The improvement of claim 22 wherein
   a) the soft connecting member is secured to the third bone anchor.

29. In a medical implant assembly having at least first, second and third bone attachment structures cooperating with a longitudinal connecting member, the improvement wherein the connecting member comprises:
   a) an elastic portion and a stiff portion with the elastic portion under pre-tension when the longitudinal connecting member is joined with the bone attachment structures; and
   b) a transition portion disposed between the stiff portion and elastic portion and located between a second and a third bone attachment structure, the transition portion having:
      i) at least one cord positioned within an opening in an end of a substantially rigid portion of the connecting member, wherein the rigid portion is secured to the first bone attachment structure; and
      ii) at least one outer sleeve at least partially surrounding the cord and overlapping at least a portion of the transition portion, and positioned between the second and third bone attachment structures.

30. The improvement of claims 29 wherein
   a) the rigid portion is a first rigid portion having at least a first opening; and further comprising:
   b) a second rigid portion having a first width; wherein
   c) the first width is secured to the first bone attachment structure.

31. The improvement of claims 29 wherein
   a) the cord has a second width less than the first width of the second rigid portion.

32. The improvement of claims 29 wherein
   a) the rigid portion has a plurality of apertures; and further comprising:
   b) a plurality of ties, each tie extending through an aperture.

33. The improvement of claims 29 wherein
   a) the rigid portion is an elongate rod.

34. The improvement of claims 29, further comprising:
   a) a plurality of ties attached to the at least one cord, each tie extending through an aperture of the rigid portion.

35. Previously Presented) The improvement of claims 29, further comprising:
- a) an outer sleeve covering the transition portion.

36. The improvement of claims 35 wherein
- a) the outer sleeve extends between and makes contact with at least two of the bone attachment structures.

37. The improvement of claims 36 wherein
- a) the outer sleeve is compressed during installation.

38. The improvement of claims 36 wherein
- a) the outer sleeve has at least one groove formed in an outer surface thereof.

39. In a medical spinal implant assembly having at least two bone anchors cooperating with a longitudinal connecting member, the improvement wherein the connecting member comprises:
- a) a substantially stiff connecting member portion secured to a first of the at least two bone anchors;
- b) an elastic soft connecting member portion extending through a second of the at least two bone anchors, the soft member having an end; the soft member being under pre-tension when joined to the bone anchors;
- c) a transition portion at least partially disposed between the at least two bone anchors and extending exterior of at least one of the bone anchors, the transition portion comprising a connection of the soft member end to the stiff connecting member portion; and
- d) an outer sleeve member disposed between the at least two bone anchors and having compressive contact with the transition portion exterior of at least one of the bone anchors during stabilization of a spinal motion segment of the spine; wherein
- e) the soft connecting member portion, when tensioned, cooperates with the second bone anchor so as to compress the outer sleeve and operably stabilize the spinal motion segment.

40. In a medical implant assembly having at least two bone attachment structures cooperating with a longitudinal connecting member joined to the bone attachment structures, the improvement wherein the connecting member comprises:
- a) a rigid portion and an elastic portion wherein the elastic portion is under pre-tension when the connecting member is joined to the bone attachment structures; and
- b) a transition portion at least partially disposed between the at least two bone attachment structures, the transition portion having
  - i) at least one substantially elongate rigid portion with at least one aperture approximate at least one end of the rigid portion; and
  - ii) at least one elongate tensionable cord member positioned within the aperture and fixed thereto, thereby defining a connection between the rigid portion and the elastic portion; wherein
  - iii) a compressible outer sleeve engages the transition portion so as to hold the outer sleeve in compression when the elastic portion is in tension, and wherein
  - iv) the connection is positioned adjacent one of the at least two bone attachment structures.

41. In a medical implant assembly having at least two bone attachment structures cooperating with a longitudinal connecting member joined to the bone attachment structures, the improvement wherein the connecting member comprises:
- a) a stiff portion joined to an elastic portion at a transition portion wherein the elastic portion is pre-tensioned when the connecting member is joined to the bone attachment structures; and
- b) the transition portion being at least partially disposed between the bone attachment structures, the transition portion having
  - i) at least one substantially elongate rigid portion with an end having at least one aperture approximate thereto, the rigid portion being connected to one of the at least two bone attachment structure; and
  - ii) at least one elongate tensionable cord member positioned within the aperture and fixed thereto, thereby defining a connection between the rigid portion and the cord member; wherein
  - iii) a compressible outer sleeve, when in use, engages the transition portion to hold the outer sleeve in compression when the cord member is tensioned, and wherein
  - iv) the connection is positioned adjacent one of the at least two bone attachment structures and co-aligned.

42. In a medical implant assembly having at least two bone attachment structures cooperating with a longitudinal connecting member, the improvement wherein the connecting member comprises:
- a) a transition portion at least partially disposed between the at least two bone attachment structures, the transition portion having
  - i) at least one substantially elongate rigid portion with at least one aperture approximate at least one end of the rigid portion; and
  - ii) at least one elongate tensionable cord member positioned within the aperture and fixed thereto; wherein
  - iii) a compressible outer sleeve engages the transition portion to hold the outer sleeve in compression when the cord member is tensioned; and wherein
- b) the at least one substantially rigid portion is a first rigid portion and further comprising a second rigid portion; and wherein
- c) both the first and second rigid portions have a plurality of apertures and further comprising a plurality of cord members, each cord member extending through one aperture of the first rigid portion and one aperture of the second portion, the cord member forming a discrete loop.

* * * * *